United States Patent
Bewick-Sonntag et al.

(10) Patent No.: US 12,193,923 B2
(45) Date of Patent: Jan. 14, 2025

(54) ABSORBENT STRUCTURE COMPRISING CO-FORMED LAYER

(71) Applicant: The Procter & Gamble Company, Cincinnati, OH (US)

(72) Inventors: Christopher Philip Bewick-Sonntag, Cincinnati, OH (US); John Daniel Algers, Montgomery, OH (US); John David Norcom, Cincinnati, OH (US); Michael Joseph Page, Cincinnati, OH (US); Shirdish Poondru, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 374 days.

(21) Appl. No.: 17/511,617

(22) Filed: Oct. 27, 2021

(65) Prior Publication Data
US 2022/0133555 A1 May 5, 2022

Related U.S. Application Data

(60) Provisional application No. 63/107,690, filed on Oct. 30, 2020.

(51) Int. Cl.
*A61F 13/15* (2006.01)
*A61F 13/537* (2006.01)
*A61F 13/53* (2006.01)

(52) U.S. Cl.
CPC .. *A61F 13/53713* (2013.01); *A61F 13/53747* (2013.01); *A61F 2013/15373* (2013.01);
(Continued)

(58) Field of Classification Search
CPC ........ A61F 13/537113; A61F 13/53747; A61F 2013/15373; A61F 2013/15967;
(Continued)

(56) References Cited

U.S. PATENT DOCUMENTS

| | | | | |
|---|---|---|---|---|
| 4,100,324 A | * | 7/1978 | Anderson | D04H 1/56 428/326 |
| 2003/0200991 A1 | * | 10/2003 | Keck | A47L 13/20 15/228 |

(Continued)

FOREIGN PATENT DOCUMENTS

| EP | 0212618 A1 | 3/1987 |
|---|---|---|
| GB | 2503529 A | 1/2014 |

OTHER PUBLICATIONS

PCT Search Report and Written Opinion for PCT/US2021/056739 dated Feb. 18, 2022, 17 pages.

*Primary Examiner* — Jacqueline F Stephens
(74) *Attorney, Agent, or Firm* — Sarah M. DeCristofaro; William E. Gallagher

(57) ABSTRACT

An absorbent structure is disclosed, which may be or form part of an absorbent core of an absorbent article. The structure has a caliper, a fluid-receiving side and a non-receiving side. The non-receiving side occupies a first x-y plane; the receiving side occupies a second x-y plane. The structure has a first zone constituting a first portion of the caliper proximate the non-receiving side, and a second zone constituting a second portion of the caliper proximate the receiving side. Each of the zones includes a co-formed blend of constituents. The blend may include AGM particles, spun filaments and/or cellulose fibers. In examples including AGM particles, particles in the first zone may have an average particle size smaller than that of particles in the second zone. In examples including filaments, filaments in the first zone may have an average filament size smaller than that of the filaments in the second zone.

11 Claims, 8 Drawing Sheets

(52) U.S. Cl.
CPC ............... *A61F 2013/15967* (2013.01); *A61F 2013/530226* (2013.01); *A61F 2013/530343* (2013.01); *A61F 2013/530489* (2013.01)

(58) Field of Classification Search
CPC ........ A61F 2013/530226; A61F 2013/530343; A61F 2013/530489
See application file for complete search history.

(56) References Cited

U.S. PATENT DOCUMENTS

| | | | |
|---|---|---|---|
| 2004/0019338 A1* | 1/2004 | Litvay | A61F 13/535 604/378 |
| 2009/0076473 A1* | 3/2009 | Kasai | A61F 13/534 604/367 |
| 2015/0342799 A1 | 12/2015 | Michiels et al. | |

* cited by examiner

ABSORBENT STRUCTURE COMPRISING CO-FORMED LAYER

CROSS REFERENCE TO RELATED APPLICATION

This application claims the benefit of U.S. Provisional Application No. 63/107,690, filed Oct. 30, 2020, the substance of which is incorporated herein by reference.

BACKGROUND

For absorbent structures such as absorbent core structures appearing in products such as (but not limited to) diapers, absorbent training pants, adult incontinence pads and pants, and feminine hygiene pads; absorbent household cleaning products, etc., it has proven advantageous to include accumulations of various constituents, alone or in combination, such as filaments or fibers spun from polymeric materials, cellulose (e.g. wood pulp) fibers, and absorbent gelling materials (also known as "superabsorbent polymers") (in fiber or particle form) (hereinafter, "AGM"). Various combinations and configurations have been designed and manufactured for purposes of balancing competing objectives of effective fluid capture and retention, absorption capacity, user/wearer comfort (e.g., dryness, softness), minimization of bulkiness (volume, caliper) (for purposes of volumetric efficiency of packaging, user/wearer comfort and discreetness under clothing), material cost, and manufacturing ease and efficiency.

Each of these types of constituent materials has various features that provide both advantages and disadvantages. For example, accumulations of filaments spun from polymers that are typically utilized tend to be resilient and provide mechanical support and shape integrity to the structure, but are not particularly absorbent. Accumulations of cellulose fibers generally have superior wicking (fluid distribution/transport) characteristics and greater absorption capacity than accumulations of polymer filaments, but are substantially less resilient, particularly when wet, and tend to cause the structure to lose shape integrity when wetted. Additionally, accumulations of cellulose fibers will release (express) absorbed fluid when pressure is applied to the structure. Cellulose fibers also tend to retain fluid on their surfaces, which if exposed to the skin of a wearer of a product including the fibers, can impart an unpleasant wet feeling to the structure. AGM particles have greater absorption capacity (per unit weight) than cellulose fibers and also resist releasing absorbed fluid under pressure (due to their osmotic mode of absorption), but do not contribute to retention of structure and shape integrity. AGM particles also do not substantially contribute to wicking (distributing or transporting) fluid through an absorbent structure. Rather, they capture fluid and swell in size as they absorb it. This makes accumulations of AGM particles, and structures including them, susceptible to "gel blocking"—wherein adjacent AGM particles in the accumulation swell with absorbed fluid, and contact, press and deform against each other, blocking fluid passageways between them and compromising the structure's ability to receive and distribute additional fluid to dry AGM particles or other dry absorbent materials at locations within the structure away from the swollen AGM particles.

With respect to feminine hygiene pads in particular (but not necessarily limited to such products), generally, it is believed that users prefer a product in which wearer-facing surface staining from fluid discharge (e.g., menstrual flow) is as small (in the x-y direction) as possible, which signals to the user that the product has rapidly drawn discharged fluid down, absorbed it into its absorbent core structure beneath the wearer-facing layer, and has contained it, rather than allowing fluid to spread across the wearer-facing layer and possibly escape the pad unabsorbed.

Attempting to take advantage of beneficial features of these typical constituent materials while mitigating their disadvantages, manufacturers of products that include absorbent structures have developed various configurations in which the absorbent structure constituents are arranged in various ways. However, currently known designs have left room for improvement in fluid absorption and retention, fluid movement along x- and y-directions along or proximate wearer-facing surfaces, absorption capacity, structural/shape integrity and user/wearer comfort.

DEFINITIONS

Figure 1:
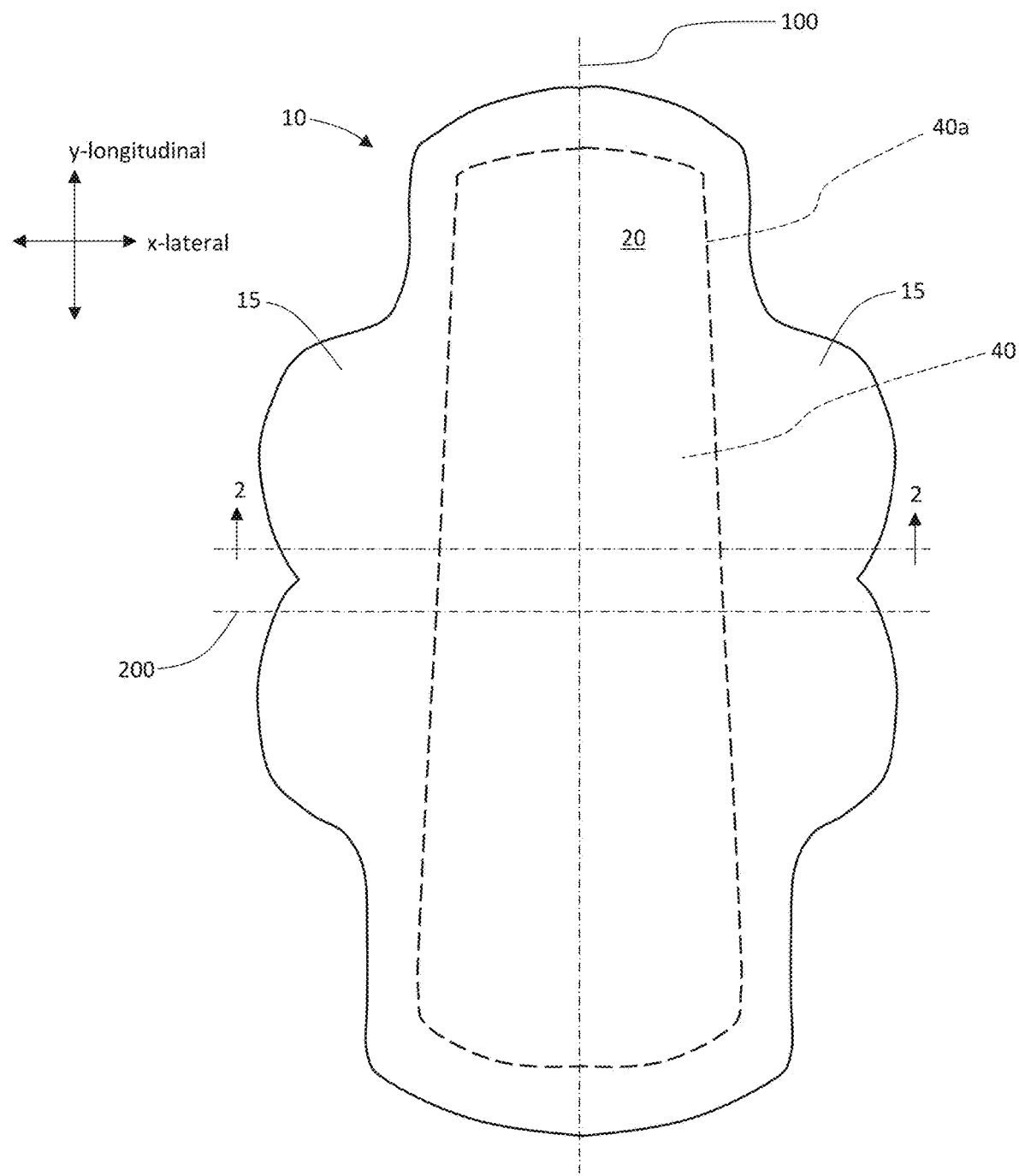
FIG. 1 is a schematic, plan view depiction of a feminine hygiene pad.

"AGM" is an abbreviation for "absorbent gelling material" (which is also known as "superabsorbent polymer,"

often abbreviated as "SAP"). AGM is a synthesized, cross-linked polymeric material that can absorb and retain, via hydrogen bonding and/or chemical absorption into its polymer chains (chemical storage) tens or even hundreds of times its own weight in aqueous fluid. AGM is currently, commonly included in ground/particulate form in a number of available absorbent products including disposable diapers, disposable absorbent training pants, disposable incontinence pads and pants, and feminine hygiene pads/sanitary napkins. AGM is now commonly (although not exclusively) made from the polymerization of acrylic acid blended with sodium hydroxide in the presence of an initiator to form a poly-acrylic acid sodium salt (sometimes referred to as sodium polyacrylate). Other non-limiting examples of materials that may be used to make AGM include as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile and biological blood binding agents such as alginates. Current manufacturing sources of AGMs suitable for use in the absorbent structures described herein include (but are not limited to) Nippon Shokubai (Osaka, Japan), BASF (Ludwigshafen (on the Rhine), Germany) and Evonik Industries (Essen, North Rhine-Westphalia, Germany).

As used herein, an "absorbent structure" is a structure that when laid out on a horizontal surface defining a plane extending in x- and y-directions, will assume a generally flat 3-dimensional shape having first and second oppositely-facing surfaces that each generally, approximately occupy respective parallel horizontal planes along the x- and y-directions, and having a caliper measured in a z-direction orthogonal to the x- and y-directions; wherein the structure includes one or any combination of fibers, filaments, open-celled foam and particles in an arrangement configured to be capable of receiving, drawing in and holding a quantity of aqueous fluid within the structure. The term includes, by way of example but not limitation, absorbent core structures (or layer components thereof) appearing in products such as diapers, absorbent training pants, adult incontinence pads and pants, and feminine hygiene pads; absorbent household cleaning products, etc. Consistent with the design of the product in which it appears, an "absorbent structure" as defined herein has a fluid receiving side coincident with one of the first and second surfaces, and a non-receiving side opposite the fluid receiving side. In products such as diapers, feminine hygiene pads and other products designed to be worn about the body to absorb bodily exudates, the fluid receiving side of the absorbent structure is proximate the wearer-facing surface of the product, and the non-receiving side is proximate the outward-facing surface of the product.

"Fiber" as used herein means an elongate body having a finite length no greater than about 5.08 cm (2 in.) Pulp fibers, for example wood pulp fibers, typically exhibit a length of from about 0.7 mm to about 2.5 mm. Fibers are often described as discontinuous in nature. Non-limiting examples of fibers include pulp fibers, such as wood pulp fibers, and synthetic staple fibers such as polypropylene, polyethylene, polyester, copolymers thereof, rayon, lyocell, glass and polyvinyl alcohol, fibers. Staple fibers may be produced by spinning filaments and then cutting the filaments into segments of a length no greater than about 5.08 cm (2 in.) thus producing staple fibers.

"Filament" as used herein means an elongate body of any length greater than that of a "fiber", which is produced in a spinning process wherein a polymeric material in a flowable or plastic state is extruded through a spinneret and subsequently longitudinally drawn and/or attenuated to reduce it to a desired filament size prior to solidification of the polymeric material via cooling, curing, drying, etc. Due to their relatively much greater and indefinite lengths as compared with "fibers," filaments are sometimes described as "continuous" in nature, but are not of infinite length in actuality. Non-limiting examples of filaments include melt-blown and/or spunbond filaments. Non-limiting examples of polymers that can be spun into filaments include natural polymers, such as starch, starch derivatives, regenerated cellulose (such as rayon, viscose and/or lyocell), cellulose derivatives, hemicellulose, hemicellulose derivatives, and synthetic polymers including, but not limited to polyvinyl alcohol and/or polyvinyl alcohol derivatives, thermoplastic polymers such as polyesters, nylons, polyolefins such as polypropylene, polyethylene, and biodegradable or compostable thermoplastics such as polylactic acid, polyhydroxyalkanoate, polyesteramide, and polycaprolactone. A filament may be monocomponent or multicomponent, e.g., bicomponent.

With respect to a layer or web component of a diaper, feminine hygiene pad or other product designed to be worn about the body to absorb bodily exudates, or the product itself, the "wearer-facing" side or surface of the component or product is the side or surface closest to the wearer when the product is normally worn, and the "outward-facing" side or surface of the component or product is the side or surface furthest from the wearer when the product is normally worn.

"Particle size" as used herein refers to the largest observable straight-line dimension of a regularly- or irregularly-shaped particle. The "average particle size" of particles within a zone of an absorbent structure is the average of the sizes of the individual particles entirely present within the zone. The sizes of the individual particles within the zone and the average thereof may be measured and calculated using any suitable sampling and measurement techniques, and calculation methods known and deemed appropriate for use in the art (including but not limited to techniques and methods described in co-pending application No. 63/107,648 (hereinafter referred to as "Algers et al.," which is incorporated by reference herein, to the extent not inconsistent herewith).

"Filament size" as used herein refers to the largest observable straight-line dimension of a portion of a filament within a selected sample, along a direction perpendicular to the greater length of the filament, i.e., along a direction perpendicular to the direction in which the filament was spun. For example, for a filament having a circular cross section, the size of the filament is the diameter of the circle. The "average filament size" of filaments within a zone of an absorbent structure is the average of the sizes of the individual filaments partially or entirely present within the zone. The sizes of the individual filaments within the zone and the average thereof may be measured and calculated using any suitable sampling and measurement techniques, and calculation methods known and deemed appropriate for use in the art (including but not limited to techniques and methods described in Algers et al.).

"Fiber size" as used herein refers the largest observable straight-line dimension of a fiber (observable without forcibly straightening the fiber to measure it). For example, the size of a curled fiber with a length that traces, roughly, an arc shape, will be the straight-line distance between the ends, measured without straightening the fiber. The "average fiber size" of fibers within a zone of an absorbent structure is the average of the sizes of the fibers entirely present within the zone. The sizes of the individual fibers within the zone and the average thereof may be measured and calculated using any suitable sampling and measurement techniques, and calculation methods known and deemed appropriate for use in the art (including but not limited to techniques and methods described in Algers et al.).

"Numerical density" with respect to particles, filaments or fibers within a zone, refers to the number of such particles, filaments or fibers within the zone, divided by the volume of the zone. For purposes herein, numerical density may be measured by counting the number of such particles, filaments or fibers present within the zone, wherein only particles and fibers entirely present within the zone are counted, and wherein filaments at least partially within the zone are counted.

As used herein, the abbreviation "gsm" means grams/meter$^2$. It is a unit used to express basis weight of a web material, customarily used in the fields of web material manufacture and processing, or its use as a subcomponent of other manufactured articles. One gsm=1 gram per square meter surface area of the web material on one of its two opposing major macroscopic surfaces. A "web material" may be a polymeric film, a nonwoven fabric (herein "nonwoven"), a woven or knitted fabric, a paper sheet material, or any combination or laminate thereof. The weight quantity of a coating, liquid additive or treatment material applied to a web material may also be expressed in gsm.

With respect to components of an absorbent article configured to be worn on the body for purposes of absorbing bodily exudates, the relative terms "top" and "upper" refer to portions more proximate the wearer-facing surface of the article, and the relative terms "bottom" and "lower" refer to portions more proximate the outward-facing surface of the article. Similarly, when a first component or feature is said to be "above" a second component or feature, the first component or feature is disposed relatively closer to the wearer-facing surface of the article than the second component or feature; and the second component or feature is "below" the first component or feature. Similarly, when a first component or feature is said to be "superadjacent" a second component or feature, the first component or feature is disposed immediately above the second component or feature (with no components or features between them); and the second component or feature is "subjacent" the first component or feature.

With respect to a web material in a flattened and unfolded condition resting on a horizontal planar surface, and with respect to an absorbent structure or absorbent article resting on a horizontal planar surface with major macroscopic surfaces of its major constituent layers in a flattened and unfolded condition occupying planes substantially parallel the planar surface, the x- and y-directions are 90 degrees from one another and oriented parallel to the planar surface, and the z-direction is orthogonal to the x- and y-directions, perpendicular to the planar surface. For purposes herein the y-direction, of a feminine hygiene pad or other absorbent article configured to be worn about a user's lower torso through the user's crotch area, will be parallel the longitudinal direction as defined herein; the x-direction will be parallel the lateral direction as defined herein; and the z-direction will be orthogonal to the longitudinal and lateral directions as defined herein. The caliper of a web material, absorbent structure or absorbent article is measured along the z-direction.

With respect to a feminine hygiene pad, or other absorbent article configured to be worn about a user's lower torso through the user's crotch area, that is opened and laid out flat on a horizontal planar surface, "lateral" refers to a direction perpendicular to the longitudinal direction and parallel the horizontal planar surface.

With respect to a feminine hygiene pad, or other absorbent article configured to be worn about a user's lower torso through the user's crotch area, that is opened and laid out flat on a horizontal planar surface and having a length measured from its forwardmost end to its rearwardmost end (as the product would be worn used normally by a user), "longitudinal" refers to a direction parallel with the line along which the length is measured, and parallel to the horizontal planar surface. "Length" refers to a dimension measured in the longitudinal direction.

With respect to a feminine hygiene pad, or other absorbent article configured to be worn about a user's lower torso through the user's crotch area, the terms "front," "rear," "forward" and "rearward" relate to features or regions of the pad corresponding to the position it would occupy as normally worn by a user, with respect to the front and rear of the user's body when standing.

When a feminine hygiene pad, or other absorbent article configured to be worn about a user's lower torso through the user's crotch area, is being worn by a user (and thus has been urged into a curved configuration), "z-direction" at any particular point location on the article refers to a direction normal to the wearer-facing surface of the pad at the particular point location. With respect to a web during its manufacture or processing, "z-direction" refers to a direction orthogonal to both the machine direction and the cross direction of manufacture or processing, and any plane parallel to the machine direction and cross direction may be referred to as an "x-y plane".

With respect to a continuous manufacturing line, the terms "upstream" and "downstream" are relative terms that positionally relate locations of items of equipment or processes on the line, relative a general path of movement of materials and/or products along the line. Materials and/or products move along the line from an upstream location to a downstream location.

Description

General

The following description focuses on a feminine hygiene pad by way of non-limiting example of a product in which absorbent structures within contemplation of the present disclosure may be included. It will be understood, however, that other absorbent articles such as but not limited to diapers, absorbent training pants, adult incontinence pads and pants, absorbent household cleaning products, etc., may include absorbent structures within contemplation of the present disclosure. Consistent with the design of the product type in which it appears, an absorbent structure as described herein has a fluid receiving side that will encounter fluid to be absorbed immediately or shortly after discharge or other exposure thereto, and an oppositely-disposed non-receiving side that will in use face away from the discharge or other exposure. By way of non-limiting example, in products such as diapers, feminine hygiene pads and other products designed to be worn about the body to absorb bodily exudates, the fluid receiving side of the absorbent structure is proximate the wearer-facing surface of the product, and the non-receiving side is proximate the outward-facing surface of the product. By way of further non-limiting example, in products such as floor cleaning pads and other surface cleaning products, the fluid receiving side is proximate the side of the product configured to contact the surface to be cleaned (e.g., a floor surface), and the non-receiving side is proximate the surface of the product that faces away from the surface to be cleaned.

Figure 2A:
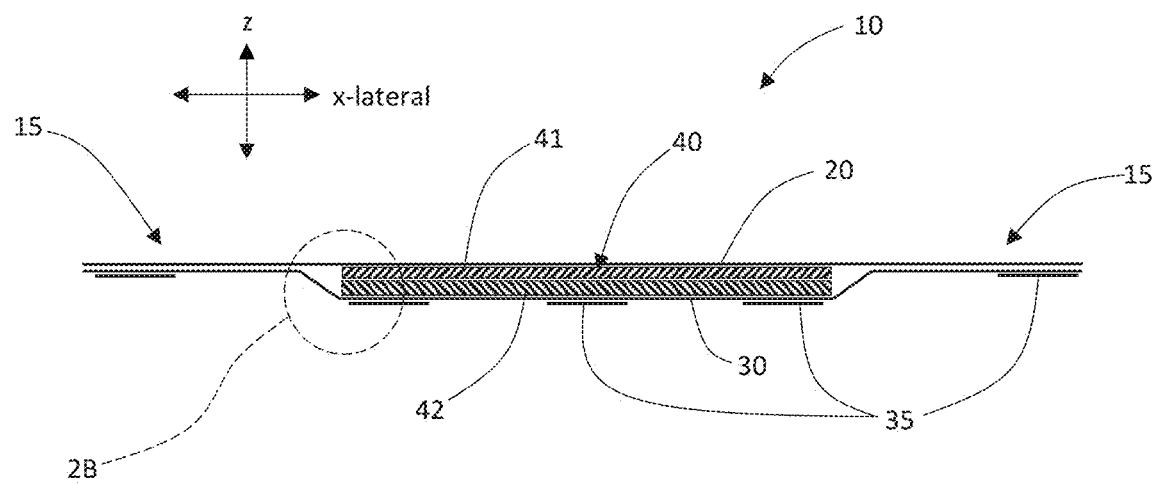
FIG. 2A is a schematic, lateral cross section of the feminine hygiene pad of FIG. 1, taken through line 2-2 in FIG. 1.

Referring to FIGS. 1 and 2A, an absorbent article such as, by way of non-limiting example, feminine hygiene pad 10, may include a liquid permeable topsheet 20, a liquid impermeable backsheet 30 and an absorbent core structure 40 disposed between the topsheet and the backsheet. The absorbent core structure has an outer perimeter edge 40a. In regions outside the outer perimeter edge 40a, the topsheet and the backsheet may be bonded together in laminated fashion by any suitable mechanism including but not limited to adhesive bonding, thermal bonding, pressure bonding, etc., thereby enveloping the absorbent core structure 40 between the topsheet 20 and the backsheet 30. Pad 10 may include opposing wing portions 15 extending laterally outside of perimeter edge 40a by a comparatively greater width dimension than the main portion of the pad. The outer surface of the backsheet forming the undersides of the main portion and the wing portions may have deposits of adhesive 35 thereon. Adhesive deposits 35 may be provided to enable the user to adhere the pad to the inside of her underpants in the crotch region thereof, and wrap the wing portions through and around the inside edges of the leg openings of the underpants and adhere them to the outside/underside of the underpants in the crotch region, providing supplemental holding support and helping protect the leg edges of the underpants from soiling by exudates. When pad 10 is packaged, adhesive deposits 35 may be covered by one or more sheets of release film or paper (not shown) that covers/shields the adhesive deposits 35 from contact with other surfaces until the user is ready to remove the release film or paper and place the pad in the underpants for use.

In some examples, absorbent core structure 40 may include a plurality of sublayers or substructures. For example, as suggested in FIGS. 2A and 2B, an absorbent core structure 40 may include an acquisition layer 41 (sometimes known as a "secondary topsheet"), configured to wick fluid from the primary location of discharge of fluid onto the product, along any or all of the x-, y-, and z-directions, thereby distributing the fluid to and along an underlying absorbent structure 42. In some circumstances this may enable more effective absorption and retention of fluid via more complete utilization of the structure and materials of absorbent structure 42.

Other absorbent articles such as, but not limited to, diapers, absorbent training pants, and adult incontinence pads and pants, also may include a topsheet and backsheet, with the absorbent structure within contemplation of the present disclosure disposed therebetween.

Topsheet

A topsheet 20 may positioned superadjacent a wearer-facing surface of the absorbent core structure 40 and may be joined thereto and to the backsheet 30 by any suitable attachment methods (not shown) known in the art. The topsheet 20 and the backsheet 30 may be joined directly to each other in the peripheral region of the pad 10 (i.e., the portion surrounding the absorbent core structure 40 in the x-y directions), and may also be indirectly joined together by directly joining them to the absorbent core structure 40 or additional optional layers within the chassis such as an acquisition layer which spans the entire or partial area of the article. This indirect or direct joining may be accomplished by any suitable attachment methods known in the art.

The topsheet 20 may be formed of any known or otherwise effective web material, such as one which is compliant, soft feeling, and non-irritating to a wearer's skin. Suitable topsheet materials include any liquid pervious material that when placed in contact with the body of the wearer will permit bodily discharges to pass from the wearer-facing surface to the outward-facing surface of the topsheet. The topsheet, in addition to being configured to allow movement of fluid through it, may also provide for the transfer or migration of lotion composition onto a wearer's skin. A suitable topsheet can be made of various materials such as woven and nonwoven materials; apertured film materials including apertured formed thermoplastic films, apertured plastic films, and fiber-entangled apertured films; hydroformed thermoplastic films; porous foams; reticulated foams; reticulated thermoplastic films; thermoplastic scrims; or combinations thereof.

Apertured film materials suitable for use to form a topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. Nos. 3,929,135; 4,324,246; 4,342,314; 4,463,045; 5,006,394; 4,609,518; and U.S. Pat. No. 4,629,643. Commercially available formed filmed topsheets include those topsheet materials marketed by the Procter & Gamble Company (Cincinnati, Ohio) under the trade name/trademark DRI-WEAVE.

Other nonlimiting examples suitable for use to form a topsheet may include woven and nonwoven materials, including fibrous materials made from natural fibers, modified natural fibers, synthetic fibers, or combinations thereof. These fibrous materials can be either hydrophilic or hydrophobic, but it is preferable that the topsheet be at least partially hydrophobic or rendered at least partially hydrophobic. As an option, portions of the topsheet can be rendered hydrophilic, using any known method for making topsheets containing hydrophilic constituents. One such method includes treating an apertured film component of a nonwoven/apertured thermoplastic formed film topsheet with a surfactant as described in U.S. Pat. No. 4,950,264. Other suitable methods and processes for treating the topsheet with a surfactant are described in U.S. Pat. Nos. 4,988,344 and 4,988,345. The topsheet may include hydrophilic fibers, hydrophobic fibers, or combinations thereof.

A particularly suitable topsheet may include staple-length polypropylene fibers having a denier of about 1.5, such as Hercules type 151 polypropylene marketed by Hercules, Inc. of Wilmington, Delaware. As used herein, the term "staple-length fibers" refers to those fibers having a length of at least about 15.9 mm (0.62 inches).

When the topsheet includes or is formed of a nonwoven fibrous material in the form of a nonwoven web, the nonwoven web may be produced by any known procedure for making nonwoven webs, nonlimiting examples of which include spunbond processes, carding, wet-laying, air-laying, meltblowing, needle-punching, mechanical entangling, thermo-mechanical entangling, and spunlacing or hydroentangling. A specific example of a suitable meltblowing process is disclosed in U.S. Pat. No. 3,978,185. The nonwoven may be compression resistant as described in U.S. Pat. No. 7,785,690. The nonwoven web may be manufactured to have loops as described in U.S. Pat. No. 7,838,099.

Other suitable nonwoven materials include low basis weight nonwovens, that is, nonwovens having a basis weight of from about 18 gsm to about 25 gsm. An example of such a nonwoven material is commercially available under the trade name P-8 from Veratec, Inc., a division of the International Paper Company in Walpole, Massachusetts. Other nonwovens are described in U.S. Pat. Nos. 5,792,404 and 5,665,452.

The topsheet may have tufts as described in U.S. Pat. Nos. 8,728,049; 7,553,532; 7,172,801; or 8,440,286. The topsheet may have an inverse textured web as described in U.S. Pat. No. 7,648,752. Tufts are also described in U.S. Pat. No. 7,410,683.

The topsheet may have a pattern of discrete hair-like fibrils as described in U.S. Pat. No. 7,655,176 or 7,402,723.

The topsheet may include one or more structurally modified zones as described in U.S. Pat. No. 8,614,365. The topsheet may include one or more out-of-plane deformations as described in U.S. Pat. No. 8,704,036. The topsheet may have a masking composition as described in U.S. Pat. No. 6,025,535.

Another suitable topsheet material or a topsheet material combined with an acquisition layer material may be formed from a three-dimensional substrate as described in U.S. provisional application Ser. No. 62/306,676. This three-dimensional substrate has a first surface, a second surface, and land areas, and also includes three-dimensional protrusions extending outward from the second surface of the three-dimensional substrate, wherein the three-dimensional protrusions are surrounded by the land areas. The substrate is a laminate comprising at least two layers in a face to face relationship, the second layer is a tissue layer facing outward from the second surface of the three-dimensional substrate, and the tissue layer comprises at least 80% pulp fibers by weight of the tissue layer.

The topsheet may include one or more layers, for example, a spunbond-meltblown-spunbond material. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097.

Added lateral extensibility in the absorbent article (i.e., in the topsheet and/or the backsheet) may be provided in a variety of ways. For example, either the topsheet or backsheet may be pleated by any known methods. Alternatively, all or a portion of the article (i.e., the topsheet and/or backsheet) may be made of a formed web material or a formed laminate of web materials like those described in U.S. Pat. No. 5,518,801. Such a formed web material includes distinct laterally extending regions in which the original material has been altered by embossing or another method of deformation to create a pattern of generally longitudinally oriented alternating ridges and valleys. The formed web material also includes laterally extending unaltered regions located between the laterally extending altered regions.

Acquisition Layer

As noted previously, the disposable absorbent articles of the present disclosure may comprise additional layers, one of which may include an acquisition layer 41. As mentioned previously, the acquisition layer may be separate and apart from the absorbent structure. Additionally, the acquisition layer is disposed beneath the topsheet 20 and on the wearer-facing surface of the core. In some forms, the acquisition layer may have a basis weight from about 30 gsm to about 100 gsm, from about 40 gsm to about 75 gsm, or from about 50 gsm to about 60 gsm, specifically including all values within these ranges and any ranges created thereby. In some forms, the acquisition layer may comprise a homogeneous mix of fibers.

In other forms, the acquisition layer may comprise a heterogeneous mix of fibers. For example, typically a plurality of carding machines feed a spunlace process. The types of fibers supplied to the cards may be homogeneously blended as mentioned above. Or in contrast, the types of fibers or the weight percentage of the fibers provided to the carding machines may be different. In such forms, where the types of fibers and/or the weight percentage of the fibers are varied to the carding machines, the resulting spunlaced structure may comprise a plurality of heterogeneous strata which are—after the spunlacing process—integral with one another.

For those forms where an acquisition layer comprises a plurality of heterogeneous strata, an acquisition gradient may be achieved with careful selection of the fibers within each of the stratum of the acquisition layer. For example, a first stratum—being closest in proximity to the topsheet—may include a lower amount of absorbent fiber as opposed to a stratum which is disposed further from the topsheet. In such forms, the first stratum may include from between about 20 weight percent to about 30 weight percent absorbent fiber while a stratum disposed furthest from the topsheet may include about 35 percent to about 80 percent by weight absorbent fiber. In such forms, the weight percentage of the stiffening fiber may stay constant among the strata or may be varied to create a stiffness gradient in the acquisition layer in addition to the absorbency gradient. Similarly, in some forms, the resilient fibers may stay constant among the strata or may be varied to create a permeability gradient in the acquisition layer in addition to the absorbency gradient or in addition to the stiffness gradient. Forms are contemplated where the acquisition layers of the present disclosure comprise between 2 to 4 strata.

Some exemplary fibers that may be included in the acquisition layer may include absorbent fibers, stiffening fibers, and resilient fibers. Forms are contemplated where at least one of the absorbent fibers, stiffening fibers, and/or resilient fibers comprise a hydrophilic coating. Suitable hydrophilic coatings are known in the art. Additionally, in some forms, the one or more of the above fibers of the acquisition layer may comprise a staple length, e.g. about 38 mm.

Any suitable absorbent fibers may be utilized. Conventional absorbent fibers include cotton, rayon or regenerated cellulose. In some specific forms, the acquisition layer may comprise viscose fibers. Due to the proximity of the acquisition layer to the topsheet, the absorbent fibers can help to draw discharged fluid from the topsheet into the absorbent core structure disposed beneath the acquisition layer. In some forms, the acquisition layer may comprise from about 20 percent to about 50 percent by weight, from about 21 percent to about 40 percent by weight, from about 25 percent to about 30 percent by weight, specifically including any values within these ranges and any ranges created thereby. In one specific form, the acquisition layer may comprise about 25 percent by weight absorbent fibers.

A higher weight percentage of absorbent fibers may be beneficial for fluid insults that are more viscous, e.g. menstrual fluid. However, the inclusion of a higher weight percentage of absorbent fibers can negatively impact resiliency and stiffness of the acquisition layer. And, too low of a weight percentage of absorbent fibers can result in a more 'wet feeling' topsheet which can create a negative impression of the product in consumers' minds. The weight percentages provided above may also work well in the context of urinary fluid insults.

Any suitable size of absorbent fiber may be utilized. A suitable measure of size can be linked to linear density. In some forms, the absorbent fiber linear density may range from about 2 dtex to about 4 dtex, about 2.5 dtex to about 3.7 dtex, or from about 2.8 dtex to about 3.5 dtex, specifically reciting all values within these ranges and any ranges created thereby. In one specific form, the absorbent fiber may comprise a dtex of about 3.3.

The absorbent fibers may have any suitable shape. In some forms, a trilobal shape may be utilized. The trilobal shape can improve wicking and improve masking. Trilobal rayon is available from Kelheim Fibres and sold under the trade name Galaxy.

In addition to absorbent fibers, as mentioned previously, the acquisition layer may also comprise stiffening fibers. Stiffening fibers may be utilized to help provide structural integrity to the acquisition layer web material. The stiffening fibers can help increase structural integrity of the acquisition layer in a machine direction and in a cross machine direction which facilitate web manipulation during processing of the acquisition layer for incorporation into a disposable absorbent article. For example, the acquisition layer of the present disclosure may be heat stiffened. The heat stiffening process can create a plurality of connection points amongst the stiffening fibers. In general, the higher the number of connection points, the stiffer the acquisition layer. So, while the creation of a plurality of connection points is beneficial for processability, the creation of too many connection points can lead to an acquisition layer which is uncomfortable in its respective disposable absorbent article. With that in mind, the constituent material of the stiffening fibers, the weight percentage of the stiffening fibers, and heat of processing should be carefully selected. The heat stiffening process is discussed hereafter.

With the foregoing in mind, any suitable stiffening fiber may be utilized. Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core—sheath arrangement where the polyethylene is the sheath. In some forms, monocomponent fibers may be utilized. In such forms, the constituent material of the monocomponent may comprise polypropylene.

Any suitable size of stiffening fiber may be utilized. Suitable linear densities of stiffening fiber may be from about 4 dtex to about 12 dtex, from about 4.5 dtex to about 10 dtex, or from about 5 dtex to about 7 dtex, specifically reciting all values within these ranges and any ranges created thereby. In one specific form, the stiffening fibers may comprise 5.8 dtex polyethylene/polyethylene terephthalate bi-component fibers arranged in a core and concentric sheath arrangement.

Any suitable weight percentage of stiffening fibers may be utilized in the acquisition layer as well. However, in some forms, the acquisition layer of the present disclosure may be heat treated (heat stiffened). The heat treatment can create connection points amongst the fibers of the acquisition layer. So, where there is a higher percentage of stiffening fibers, more connection points may be created. The additional connection point can yield a much stiffer acquisition layer which may negatively impact comfort. In some forms, the acquisition layer may comprise about 20 percent to about 40 percent by weight stiffening fibers or from about 25 percent to about 35 percent by weight stiffening fibers, specifically including all values within these ranges and any ranges created thereby.

As noted previously, the acquisition layer of the present disclosure may additionally comprise resilient fibers. The resilient fibers can help the acquisition layer maintain its permeability. Any suitable size fiber may be utilized. In some forms, the resilient fibers can have a linear density of about 6 dtex to about 12 dtex, from about 8 dtex to about 11 dtex, or from about 9 dtex to about 10 dtex, specifically reciting all values within these ranges and any ranges created thereby. In one specific form, the resilient fibers may have a linear density of about 10 dtex. In one specific example, the resilient fibers may comprise 10 dtex hollow spiral polyethylene terephthalate fibers.

If smaller fiber sizes are utilized, the resiliency of the acquisition layer would be expected to decrease. And, with the decreased size at the same weight percentage, a higher number of fibers per gram would equate to a decrease in permeability of the acquisition layer. Additionally, some conventional acquisition layers may utilize superabsorbent polymer, e.g. AGM, to help drain their respective topsheets. As noted previously, AGM typically swells when absorbing fluid insults and can reduce permeability of an acquisition layer by occluding openings in the acquisition layer. However, in general, conventional acquisition layers have lower permeability which helps reduce the likelihood that the AGM will occlude openings of these conventional acquisition layers upon swelling. In contrast, due to the higher permeability of the acquisition layers of the present disclosure, AGM may not be suitable for utilization therewith without additional measures ensuring that the AGM will not greatly reduce the permeability thereof. Rather, AGM may be provided in a separate layer in an absorbent article.

Any suitable weight percentage of resilient fibers may be utilized. In some forms, the acquisition layer of the present disclosure may comprise from about 25 percent to about 55 percent by weight resilient fibers, between 35 percent and 50 percent resilient fibers, or between 40 percent and 45 percent by weight resilient fibers, specifically including any values within these ranges and any ranges created thereby. In some specific forms, the acquisition layer may comprise about 45 percent by weight resilient fibers. In some specific forms, the acquisition layer may comprise about 45 percent, 10 dtex, hollow spiral polyethylene terephthalate fibers.

With regard to the heat stiffening process, any suitable temperature may be utilized. And, the suitable temperature may be impacted, in part, by the constituent chemistry of the stiffening fibers as well as by processing speed of the acquisition layer web. In some forms, the acquisition layer web may be heat stiffened at a temperature of 132 degrees Celsius. Additionally, in order to provide a uniform stiffness property across the acquisition layer web, any heating operation should be set up to provide uniform heating to the acquisition layer web. Even small variations in temperature can greatly impact the tensile strength of the acquisition layer web. For example, for two comparable acquisition layers having a basis weight of about 50 gsm, both with the above formulations, a significant difference was created with a small temperature difference. A heat stiffening process at 135 degrees C. yielded a CD direction tensile strength for one sample that was twice the CD direction tensile strength of a sample subjected to a 132 degrees C. stiffening process. A similar result was witnessed for samples having comparable compositions and about a 70 gsm basis weight. Additionally, there was about a 1.5 times difference for the MD direction tensile strength where the sample subjected to the higher temperature, i.e. 135 degrees C., had a higher tensile strength in the MD direction.

Backsheet

The backsheet 30 of the chassis 20 may be positioned beneath or subjacent an outward-facing surface of the absorbent core structure 40 and may be joined thereto by any suitable attachment mechanisms (not shown) known in the art. For example, the backsheet 30 may be secured to the absorbent core structure 40 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent core structure 40 is not joined to the backsheet 30, the topsheet 20, or both.

The backsheet 30 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 30 may prevent, or at least inhibit, the exudates absorbed and contained in the absorbent core structure 40 from wetting articles of clothing which contact the incontinence pad 10 such as undergarments. However, in some instances, the backsheet 30 may permit vapors to escape from the absorbent core structure 40 (i.e., is breathable) while in other instances the backsheet 30 may not permit vapors to escape (i.e., non-breathable). Thus, the backsheet 205 may comprise a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with structures within contemplation of the present disclosure.

The backsheet 30 acts as a barrier to any absorbed bodily fluids that may pass through the absorbent core structure 40 to the outward-facing surface thereof with a resulting reduction in risk of staining undergarments or other clothing. Further, the barrier properties of the backsheet permit manual removal, if a wearer so desires, of the interlabial absorbent article with reduced risk of hand soiling. A preferred material is a soft, smooth, compliant, liquid and vapor pervious material that provides for softness and conformability for comfort, and is low noise producing so that movement does not cause unwanted sound.

The backsheet may comprise a wet laid fibrous assembly having a temporary wet strength resin incorporated therein as described in U.S. Pat. No. 5,885,265. The backsheet may further be coated with a water resistant resinous material that causes the backsheet to become impervious to bodily fluids without impairing the spreading of adhesive materials thereon.

Another suitable backsheet material is a polyethylene film having a thickness of from about 0.012 mm (0.5 mil) to about 0.051 mm (2.0 mils). The backsheet may be embossed and/or matte finished to provide a more cloth-like appearance. Further, the backsheet may permit vapors to escape from the absorbent structure 42 (i.e., the backsheet is breathable) while still preventing body fluids from passing through the backsheet. A preferred microporous polyethylene film which is available from Tredegar Corporation, Virginia, USA, under Code No. XBF-1 12W.

For a stretchable but non-elastic backsheet, one material that can be used is a hydrophobic, stretchable, spun laced, non-woven material having a basis weight of from about 30 to 40 gsm, formed of polyethylene terephthalate or polypropylene fibers. This material is breathable, i.e. permeable to water vapor and other gases.

For an elastic backsheet, one material which can be used is an elastic film sold under the trademark EXX500 by Exxon Corporation. The material of this film is formed from an elastomeric base composition consisting of a styrene block copolymer. However, this material is not breathable. Another material which can be used for an elastic backsheet is a plastic film that has been subjected to a process that provides it with elastic-like properties without attaching elastic strands to the film, and may for example comprise a formed film made in accordance with U.S. Pat. Nos. 4,342,314 and 4,463,045.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389; GB A 2184 390; GB A 2184 391; U.S. Pat. Nos. 4,591,523; 3,989,867; 3,156,242; and WO 97/24097.

The backsheet may have two layers: a first layer comprising a gas permeable aperture formed film layer and a second layer comprising a breathable microporous film layer as described in U.S. Pat. No. 6,462,251. Suitable dual or multi-layer breathable backsheets for use herein include those exemplified in U.S. Pat. Nos. 3,881,489; 4,341,216; 4,713,068; 4,818,600; EP 203 821; EP 710 471; EP 710 472; and EP 793 952.

The backsheet may be a relatively hydrophobic, 18 gsm spunbond nonwoven web of 2 denier polypropylene fibers. The backsheet may also be a laminate as is known in the art.

The backsheet may be vapor permeable as described in U.S. Pat. Nos. 6,623,464, or 6,664,439. The backsheet can be formed from any vapor permeable material known in the art. The backsheet may be a microporous film, an apertured formed film, or other polymer film that is vapor permeable, or rendered to be vapor permeable, as is known in the art.

The backsheet may be a nonwoven web having a basis weight between about 20 gsm and about 50 gsm. In one embodiment, the backsheet is a relatively hydrophobic, 23 gsm spunbond nonwoven web of 4 denier polypropylene fibers available from Fiberweb Neuberger, under the designation F102301001. The backsheet may be coated with a non-soluble, liquid swellable material as described in U.S. Pat. No. 6,436,508.

The backsheet has an outward-facing side and an opposite wearer-facing side. The outward-facing side of the backsheet comprises a non-adhesive area and an adhesive area. The adhesive area may be provided by any conventional means. Pressure sensitive adhesives have been commonly found to work well for this purpose.

Absorbent Structure

Figure 2B:
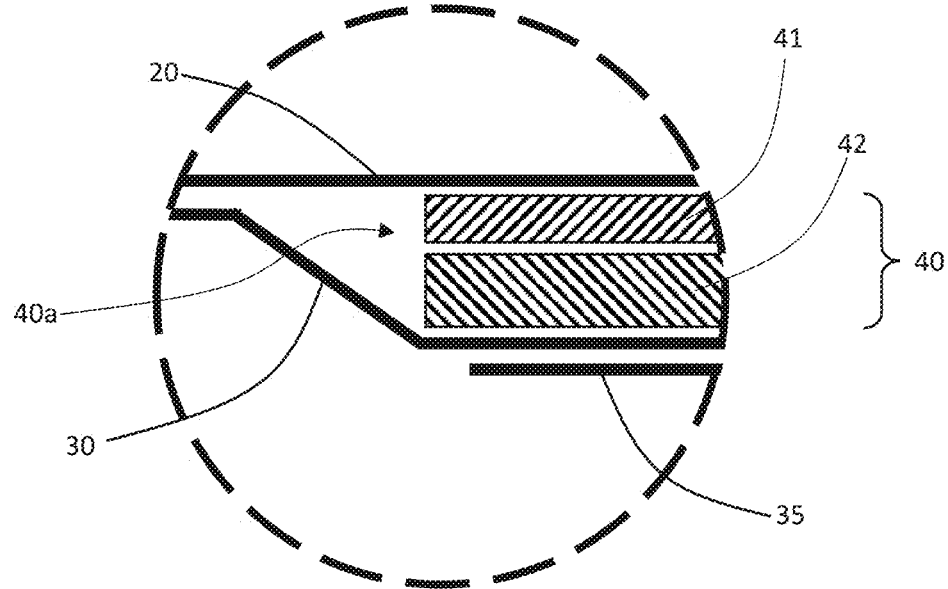
FIG. 2B is an enlarged view of a portion of FIG. 2A, shone encircled within circle 2B in FIG. 2A.

Referring to FIG. 2B, an absorbent structure 42 may be disposed within an absorbent article, and may itself constitute the absorbent core structure 40, or may be a subcomponent thereof.

It has been learned that it can be desirable to configure an absorbent core structure 40 such that upper strata thereof are capable of readily receiving and even drawing a sudden or rapid fluid discharge from overlying layers such as the topsheet and/or acquisition layer (if included), to prevent discharged fluid from escaping the article, and following receipt of the fluid, quickly distributing it to and across relatively more absorbent strata beneath. Such a configuration enables the manufacturer to provide an absorbent article such as, but not limited to, feminine hygiene pads, disposable incontinence articles, disposable diapers and disposable training pants, that is highly effective at acquiring fluid rapidly to minimize the potential for fluid escaping the article, and one that maximizes effective utilization of the absorbent materials.

The inventors have conceived a co-form manufacturing process and apparatus more fully described Algers et al., the disclosure of which is incorporated by reference herein, to the extent not inconsistent herewith. The process and apparatus can enable the manufacturer to lay down an arranged/stratified combination of spun polymeric filaments, AGM particles and cellulose fibers (or subcombinations thereof) to create an absorbent structure in a consolidated, continuous operation, that is efficient in operation and imparts the structure with several advantages.

Figure 3:
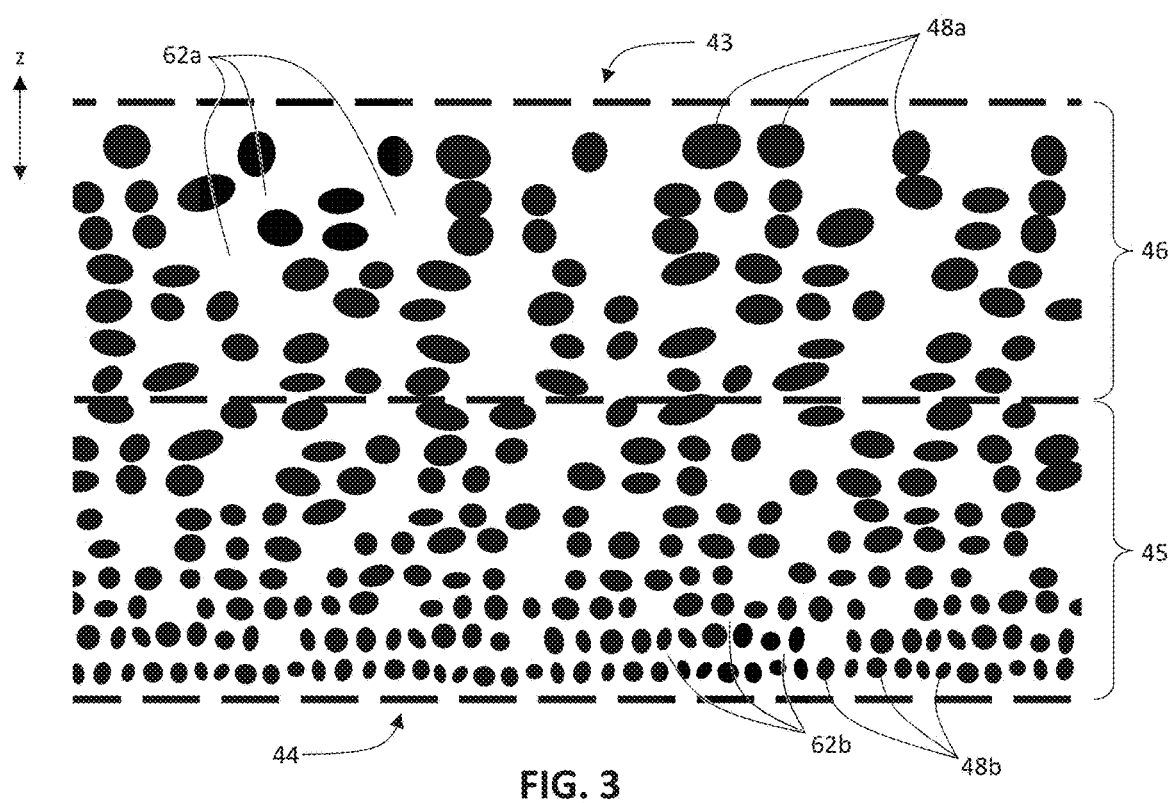
FIG. 3 is a schematic view of an arrangement of AGM particles within a portion of an absorbent structure, shown along a plane extending along a z-direction, having a variation and/or stratification in average size from a fluid receiving side to a non-receiving side of the structure.
Figure 4:
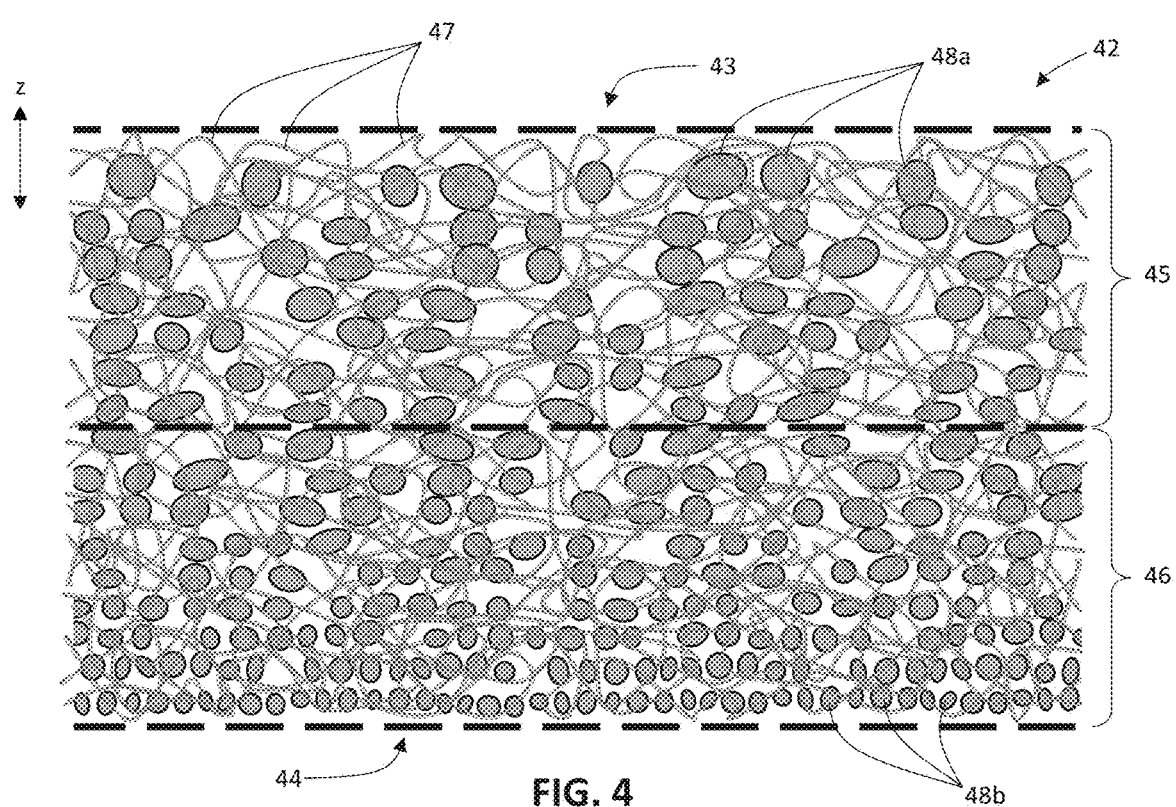
FIG. 4 is a schematic view of a combination of spun filaments and an arrangement of AGM particles within a portion of an absorbent structure, shown along a plane extending along a z-direction, the AGM particles having a variation and/or stratification in average size from a fluid receiving side to a non-receiving side of the structure.
Figure 5:
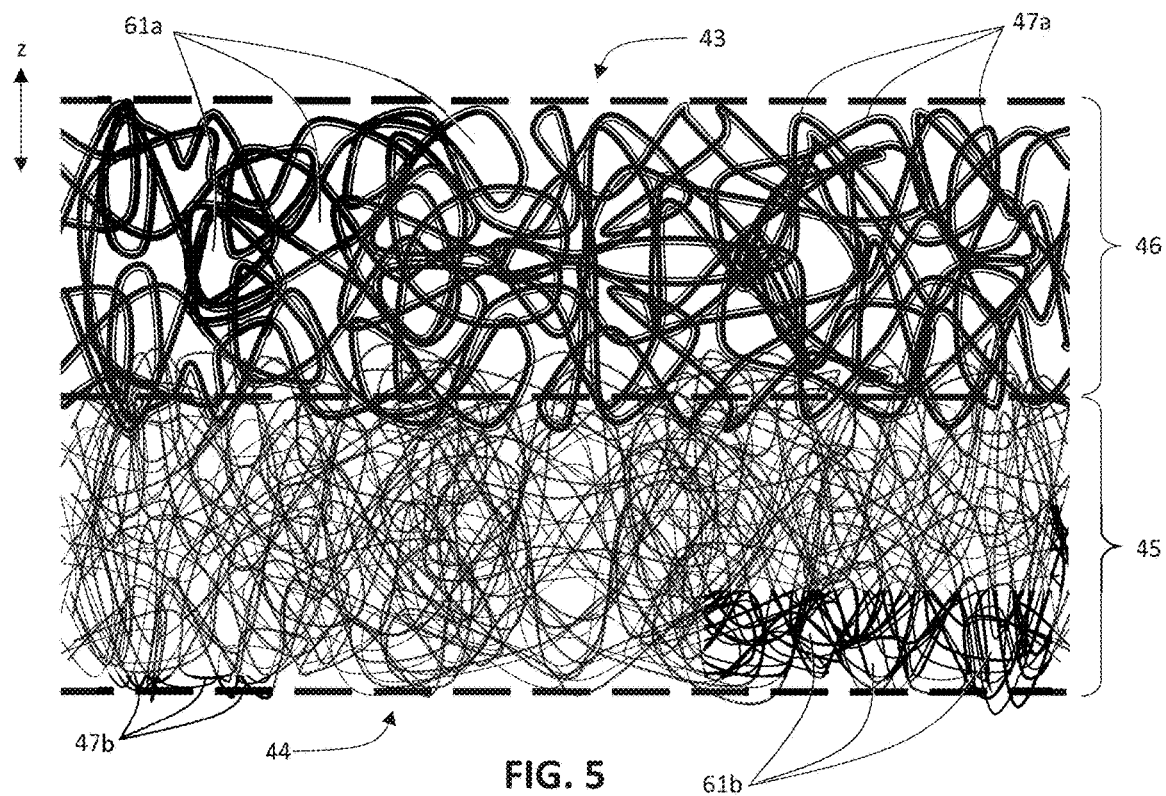
FIG. 5 is a schematic view of an arrangement of spun filaments within a portion of an absorbent structure, shown along a plane extending along a z-direction, having a variation and/or stratification in average size from a fluid receiving side to a non-receiving side of the structure.

FIGS. 3 and 5 schematically depict examples of the manners in which the described process and apparatus enable the manufacturer to stratify the respective constituents within a co-formed absorbent structure, by their size.

Figure 11:
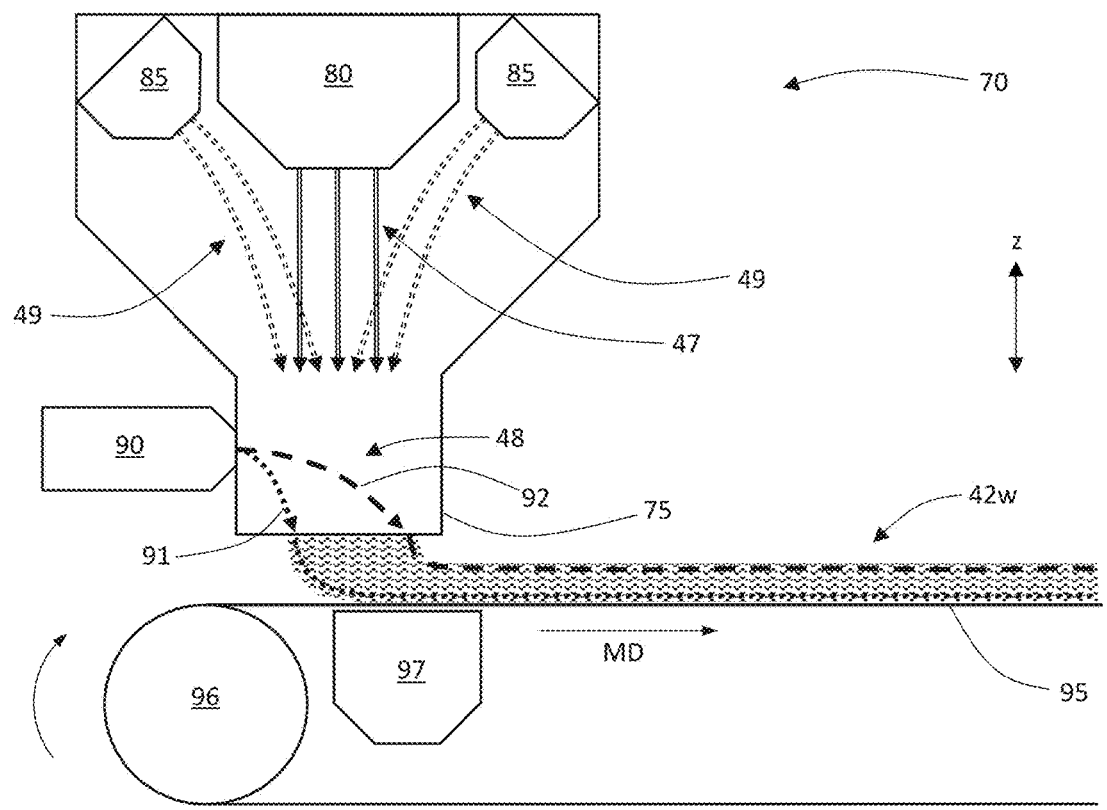
FIG. 11 is a schematic view of a co-forming box configuration disposed over a formation belt, schematically depicting operation thereof.

Referring to FIGS. 3 and 11, the referenced co-form process and apparatus enables stratification along the z-direction within a single layer, by AGM particle size. The stratification is manifest as a gradual general transition or gradient in particle size, along the z-direction, distinguishable from one or more abrupt, step-wise transition(s) as would occur in a sequential layering process configured to create layers having differing average AGM particle sizes.

AGM is commercially available in ground, particulate form, in batches wherein particles may have sizes ranging from, for example, about 45 μm to about 750 μm. Prior art co-forming processes currently known to the inventors have not enabled the manufacturer to stratify (i.e., impart a z-direction particle size gradient) to the accumulated combination of AGM particles, filaments and/or fibers forming the co-formed absorbent structure. However, referring to FIG. 11, it has been discovered that delivering a metered flow of AGM particles 48 into a mixing section 75 of a co-forming box configuration 70, wherein the particles are delivered and driven along an initial trajectory (by, e.g., an particle-entraining air stream) along a direction that is not aligned with the (e.g. vertical) main air stream carrying the fiber and/or filament constituents of the co-form structure within a co-forming box configuration 70, can have the effect of causing the particles to stratify within the main air stream and resulting accumulation of co-form structure constituents, by particle size.

A co-forming box configuration 70 may include a beam 80 for producing spun filaments 47, one or more fiber metering and delivery elements 85 for delivering cellulose fibers, and an AGM particle metering and delivery element 90, and associated airflow-driving equipment (not shown). The co-forming box configuration 70 may be positioned above a foraminous forming belt 95 cycling about two or more rollers 96 and defining a machine direction MD of manufacture of an absorbent structure. To help draw (e.g., downward) airflow through the foraminous forming belt 95 and thereby draw, accumulate and settle the air-entrained constituents 47, 48 and/or 49 onto the forming belt 95, a vacuum system 97 may be positioned beneath the belt.

As described in more detail in Algers et al., it has been observed that the individual trajectories 92 of the relatively larger particles (which have greater mass and larger Stokes numbers) in such a configuration are less rapidly influenced by the main fiber/filament air stream (e.g., downward) direction toward the forming belt 95. On the other hand, the individual trajectories 91 of the relatively smaller particles (which have lesser mass and smaller Stokes numbers) are more rapidly influenced by the main fiber/filament air stream direction toward the forming belt. Thus, in some examples such as that depicted in FIG. 11, the fiber/filament air stream direction toward the forming belt may be substantially vertical and downward, while the co-forming box may be configured such that the initial angle of delivery of the AGM particles may be non-vertical, or even substantially horizontal, and generally directed along the machine (forming belt movement) direction. This arrangement under suitably controlled operating conditions may be used to cause the paths of smaller AGM particles exiting the metering and delivery element 90 to be redirected more quickly and thereby follow shorter trajectories 91, while the paths of the larger AGM particles will be redirected more slowly and thereby follow longer trajectories 92.

Within the co-forming box configuration 70, the other constituents of the co-form blend (fibers 47 and/or filaments 49) may be blended in mixing section 75 with the stratifying AGM particles so as to reach the belt in a relatively uniform or homogeneous fiber/filament blend, forming a matrix of accumulated fibers and/or filaments that captures and retains the AGM particles in place, within accumulation 42w.

The result is that the largest AGM particles will be deposited and settle in strata more proximate one of the top and bottom sides of the accumulation 42w of constituents on the belt 95; the smallest particles will be deposited and settle in strata more proximate the other of the top and bottom sides of the accumulation 42w; and deposits of particles of sizes falling between those of the largest and smallest particles will, generally, stratify along the z-direction, by size, accordingly. Whether the largest particles are deposited in the accumulation 42w within or proximate upper strata, or within or proximate lower strata (and vice versa), will depend upon the direction of movement of the belt relative the direction of delivery of the particles by delivery element 90. In the example depicted in FIG. 11, the largest particles will be deposited within or proximate upper strata of the accumulation 42w as a consequence of the direction of machine direction MD, being the same or generally aligned with the direction of delivery of the particles. It may be appreciated that a machine direction MD opposite the direction of delivery of the particles can under suitably controlled operating conditions have the reverse effect (largest particles deposited proximate the bottom side, smallest particles deposited proximate the top side, of the accumulation 42w).

It will be appreciated that process variables such as but not limited to (1) the location of the AGM particle metering and delivery element 90 relative the mixing section 75; (2) AGM particle delivery/airflow angle and velocity relative the mixing airflow direction and velocity; (3) AGM particle delivery rate (i.e., AGM particle throughput), etc., may be adjusted to impact the extent of AGM particle size stratification that occurs, and may also be adjusted to distribute and stratify AGM particles in only selected strata along the z-direction, within a larger accumulation 42w of constituents. For example, the apparatus may be configured to distribute and stratify the AGM particles, by size, throughout substantially the entire z-direction depth of the accumulation 42w; or to create a narrower band of distribution of the AGM particles within the accumulation 42w, e.g., within strata that are centered along the z-direction, with strata of constituent filaments and/or fibers that do not include substantial quantities of AGM particles, overlying and underlying the central strata that include AGM particles; or strata including AGM particles that are more proximate the top side of the accumulation (relative the belt 95); or strata including AGM particles that are more proximate the bottom side of the accumulation (relative the belt 95).

Following accumulation as described above, the accumulation 42w of constituents may be processed in downstream operations (e.g., z-direction consolidation; bonding; cutting) to convert it into individual absorbent structures 42 for inclusion in absorbent articles of the types contemplated herein.

Thus, referring to FIG. 3, the co-forming process and apparatus may be configured such that relatively smaller-size AGM particles 48b are distributed in a first zone 45 more proximate a non-receiving side 44 of the absorbent structure, at a greater numerical density, while relatively larger-size AGM particles 48a are distributed in a second zone 46 more proximate the fluid-receiving side 43, at a lesser numerical density. The lesser numerical density of the larger particles 48a in second zone 46 will result in larger intra-particle spaces 62a between/among them, while the greater numerical density of the smaller particles 48b in first zone 45 will result in smaller intra-particle spaces 62b between/among them. (Herein, the large, straight, horizontal dashed lines appearing FIGS. 3-7 may, but do not necessarily, identify actual physical boundaries, interfaces or abrupt transitions in structure within features of an absorbent structure 42, but rather, are conceptual, used herein for purposes of illustrating identification of respective overlying/underlying zones of an absorbent structure with constituent filaments and/or particles having average sizes that are stratified/differ along a z-direction, from a non-receiving side to a receiving side of the absorbent structure. For purposes herein, the term "zone" does not necessarily imply a physical boundary, interface or abrupt transition in a structure along the z-direction. If one can identify respective distinct, overlying and underlying "zones" of any z-direction dimension within of a structure, that have the differences in features recited in the claims herein, then such zones are necessarily present.)

Figure 12:
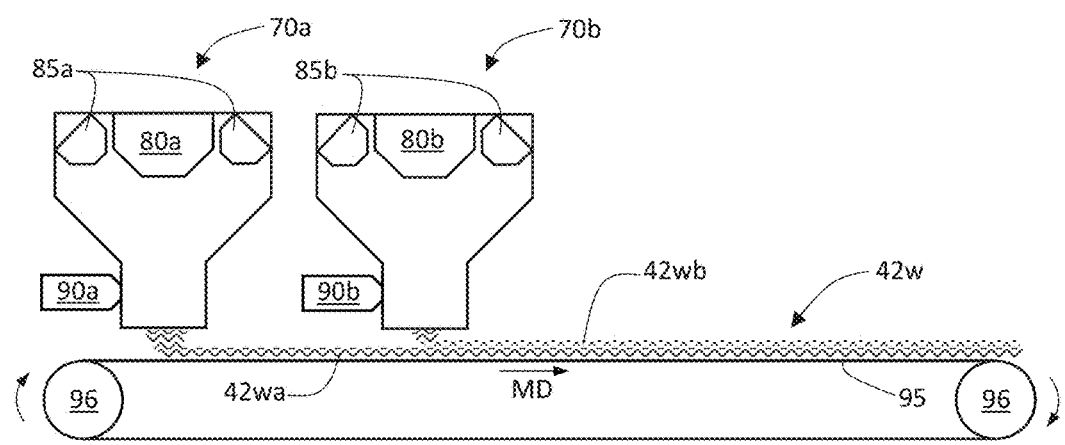
FIG. 12 is a schematic view of a series of two co-forming box configurations disposed over a formation belt, schematically depicting operation thereof.

Additionally, as reflected in FIG. 5, the co-forming process and apparatus enable the manufacturer to stratify the structure by filament size, for example, by laying down and accumulating spun filaments of a relatively smaller average size 47b in a first zone 45, and spun filaments of a relatively greater average size 47a in a second zone 46, where the second zone 46 is located more proximate a fluid-receiving side 43 of the structure, and the first zone 45 is located more proximate a non-receiving side 44 of the structure. The filaments may be spun and attenuated to the desired sizes in, for example, meltblowing equipment and processes embodied in beams 80a, 80b. Referring to FIGS. 11 and 12, the stratification may be achieved by locating at least first and second configurations of filament manufacturing equipment (beams 80a, 80b) each including a bank of spinnerets, and associated filament drawing/attenuating systems in association with a series of co-forming box configurations 70a, 70b along the manufacturing line, and controlling process variables of the respective beams 80a, 80b such as melted polymer resin throughput, spinneret size/configuration, melt temperature, filament drawing/attenuating air speed, etc. The process may be controlled wherein smaller-size filaments 47b are produced by an upstream first beam 70a and accumulated so that they are relatively greater in number per unit volume of the structure (i.e., greater filament numerical density), and the larger-size filaments 47a produced by a second beam 70b downstream of the first beam are relatively lesser in number per unit volume of the structure (i.e., lesser filament numerical density). If desired for particular circumstances, the process may be controlled to effect the reverse arrangement, i.e., wherein larger-size filaments are produced by an upstream first beam 70a and accumulated so that they are relatively fewer in number per unit volume of the structure (i.e., lesser filament numerical density), and laid down first, and smaller-size filaments produced by a second beam downstream of the first beam are relatively greater in number per unit volume of the structure (i.e., greater filament numerical density), and laid down second, over the larger-size filaments.

Figure 6:
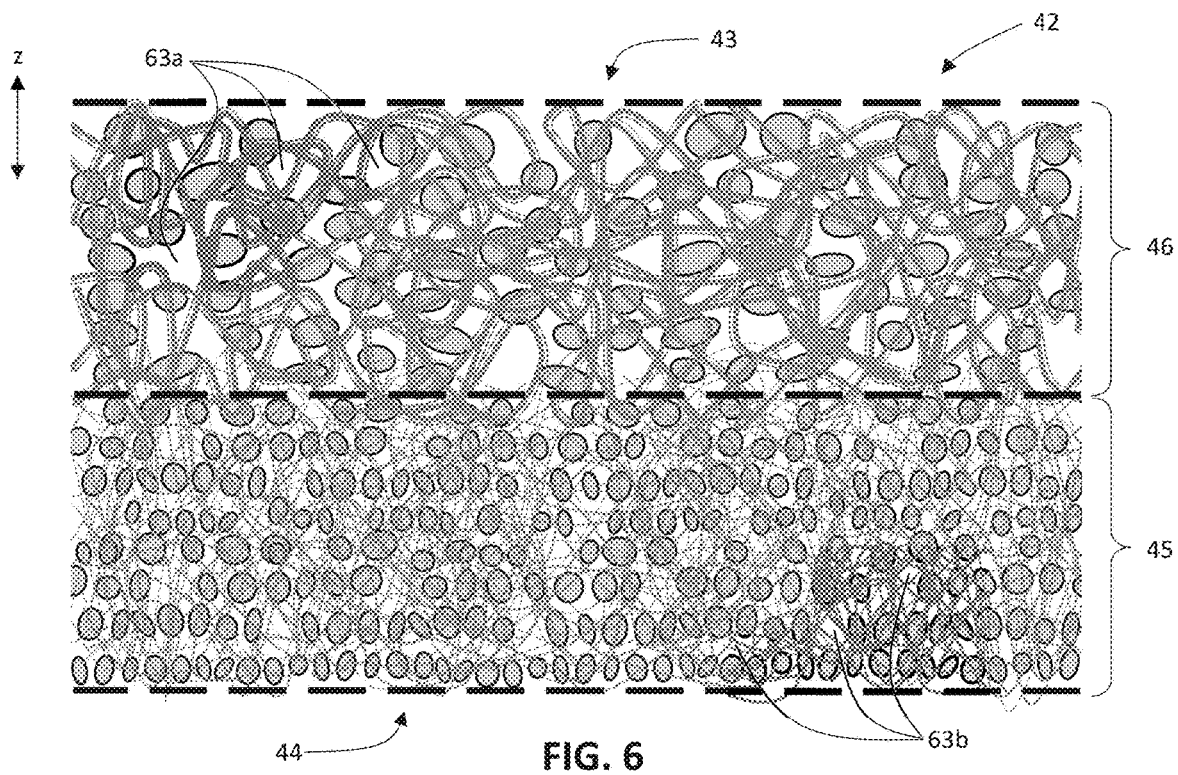
FIG. 6 is a schematic view of a combination of the arrangements shown in FIGS. 3 and 5.

Referring to FIGS. 5 and 6, where the larger 47a and smaller 47b filaments have substantially similar (or identical) polymer compositions, the larger filaments 47a will be relatively stiffer and provide a greater contribution to resilience of the structure (enhancing shape integrity and recovery after compression or bending, and wetting), while the smaller filaments 47b will be more pliable. Additionally, the process may be controlled such that the lesser numerical density of the accumulation of larger filaments 47a results in a stratum (second zone 46) having relatively larger intra-filament spaces 61a that provide fluid passageways into and through second zone 46 that make second zone 46 better configured to receive and distribute a sudden or rapid discharge of fluid to which the fluid-receiving side 43 is exposed, and hold larger-size AGM particles in place within the matrix of larger intra-filament spaces 61a created by the less numerically dense accumulation of larger filaments 47a. At the same time, the greater numerical density of the accumulation of smaller filaments 47b results in a stratum (first zone 45) with smaller intra-filament spaces 61b, making the first zone 45 better configured for slower/more controlled fluid distribution and absorption, and holding smaller-sized AGM particles in place within the matrix created by the more numerically dense accumulation of smaller filaments 47b defining a matrix of smaller intra-filament spaces 61b.

The filaments 47 may be spun from any suitable polymeric resin or combination of resins, including but not limited to polypropylene (PP), polyethylene (PE), polyethylene terephthalate (PET), combinations thereof, and any other suitable polymers known and used for producing nonwoven materials and filaments for use in absorbent articles of the types contemplated herein. The filaments may be spun and attenuated in any suitable spinning process, including but not limited to a spunbond process and a meltblowing process. In some examples, it may be desired that filaments in the second zone 46 be spun from PET, which tends to yield relatively stiffer filaments as compared to those spun from polyolefins such as polypropylene and polyethylene. This, in combination with relatively larger filament size, provides relatively stiff filaments that are useful for imparting resiliency and lasting shape integrity to the structure. In some further examples, it may be desired that filaments in the first zone 45 be spun from a polyolefin such as polypropylene, polyethylene or a combination thereof. This, in combination with relatively smaller filament size, provide for relatively relative pliable filaments that are still somewhat resilient, and enhance flexibility and contribute to providing a soft feel to the structure. In further examples, both zones may include a blended combination of filaments spun from differing polymers, including PET and a polyolefin such as polypropylene and/or polyethylene.

Filaments spun from many types of polymeric resins may have hydrophobic surfaces as a consequence of the chemistry of the polymers. As a component of an absorbent structure, an accumulation of hydrophobic filaments may be undesirable in some circumstances, because the mass of accumulated hydrophobic filaments may resist wicking, and thereby slow or obstruct aqueous fluid movement and distribution therethrough. However, in circumstances in which filaments 47 used as constituents of an absorbent structure 42 would be ordinarily hydrophobic in nature as a consequence of the polymer component(s) of the resins used for spinning, the filaments 47, or even the component resins from which they are spun, may be treated to render the filaments 47 hydrophilic. In some examples, the filaments may be treated with a hydrophilizing surface coating, following spinning. In other examples, a hydrophilizing melt additive may be added to the component resin(s) prior to spinning. This latter approach may be preferred in some circumstances in which coating the spun filaments after spinning (and, for example, after formation of the absorbent structure 42) may be impractical and/or not satisfactorily effective.

Non-limiting examples of surface treating hydrophilizing surface modifiers include surfactants, such as Triton X-100 (a product of MilliporeSigma, St. Louis, MO, currently an affiliate of Merck KGaA, Darmstadt, Germany). Non-limiting examples of hydrophilizing melt additives that may be to the polymer composition (polymer melt), such as the polypropylene melt, prior to spinning filaments, include hydrophilizing additives such as VW351 and/or S-1416 (products of Polyvel, Inc., Hammonton, NJ) and Irgasurf (a product of BASF, Ludwigshafen, Germany). The hydrophilizing modifier may be associated with the hydrophobic or non-hydrophilic material at any suitable level known in the art. In one example, the hydrophilizing modifier is associated with the polymer composition, such as the hydrophobic and/or non-hydrophilic material within the polymer composition at a level of greater than 0% to less than about 20% and/or greater than 0% to less than about 15% and/or greater than 0.1% to less than about 10% and/or greater than 0.1% to less than about 5% and/or greater than 0.5% to less than about 3% by dry weight of the hydrophobic or non-hydrophilic material. In another example, the hydrophilizing modifier may be present in the filaments at a level of from about 0.1% to about 10% and/or from about 0.5% to about 7% and/or from about 1% to about 5% by weight of the filaments.

To enable or enhance the ability to use two or more co-forming boxes arranged in series along a manufacturing line to provide a combination including both the filament size stratification and the AGM particle size stratification/gradient reflected in FIGS. 6-10, the supply of AGM particles may be sieved into, respectively, two or more average sizes prior to their delivery to the respective two or more co-forming box configurations 70a, 70b. For example, the available supply of AGM particles may be sieved into two sub-supplies of AGM particles including a first sub-supply having an average size equal to or smaller than a selected delineating (sieve) size, and a second sub-supply having an average size greater than the selected delineating (sieve) size. The sub-supply of the smaller-size particles may be introduced into the upstream co-forming box configuration 70a, whereby the smaller-size particles will be deposited first in the accumulation of co-form constituents on the forming belt 95, thereby becoming disposed in lower strata (e.g., in first zone 45) of structure 42 formed on the forming belt. The sub-supply of the larger-size particles may be introduced into the downstream co-forming box, whereby the larger-size particles will be deposited second in the accumulation of co-form constituents on the forming belt, thereby becoming disposed in upper strata (e.g., in second zone 46) formed on the forming belt.

Referring to FIGS. 11 and 12, it will be appreciated, further, that respective co-forming box configurations 70a, 70b may be configured to deliver a variety of combinations of absorbent structure constituent sizes and types to the accumulation 42w formed on forming belt 95, and strata thereof. The respective beams 80a, 80b may be configured to deliver respective filaments of like sizes or differing (i.e. smaller and larger, or vice versa) sizes. The respective beams 80a, 80b may be configured to spin filaments from the same or respectively differing materials, e.g., differing thermoplastic polymer resins. The respective AGM particle metering and introduction delivery elements 90a, 90b may be configured to deliver AGM particles of respectively differing types, average sizes, compositions, etc., as well as respectively same or differing blends thereof. The respective fiber metering and delivery elements 85a, 85b may be configured to deliver cellulose fibers of differing sizes, types, species, etc., as well as respectively same or differing blends thereof. A single co-forming box configuration 70, or one or both of respective co-forming box configurations 70a, 70b, may be configured to deliver fewer than all three, e.g., only two, of the constituents particularly discussed herein (spun filaments, fibers and AGM particles). The respective upstream and downstream sets of beams 80a, 80b, AGM particle metering and introduction delivery elements 90a, 90b, and fiber metering and delivery elements 85a, 85b may be configured to deliver their respective associated structure constituents at differing rates (e.g., by constituent material weight/minute throughput) so as to effect respective sub-accumulations 42wa, 42wb having differing weight proportions of the respective constituents.

It should be noted that FIGS. 3 and 5 are not intended to illustrate the complete composition of an absorbent structure, but only illustrate arrangements of respective AGM particle and spun filament constituents as they may be relatively positioned within an absorbent structure, using the process and apparatus disclosed in Algers et al. The referenced process and apparatus enables the arrangement of AGM particles stratified by size so as to generally exhibit a gradient of particle sizes along the z-direction, as suggested in FIG. 3, which will be maintained as the particles are held in position within matrices created by filaments 47 and/or fibers 49 in the continuous co-form process. The referenced process and apparatus enables the arrangement of filament accumulations stratified by size as suggested in FIG. 5.

Various examples of potential resulting absorbent structures are schematically depicted in FIGS. 4 and 6-10 which depict the size-stratified AGM particles, and if desired, size-stratified spun filaments as they may appear in examples of absorbent structures 42. Additionally, where two or more co-forming box configurations 70a, 70b are arranged in series along a manufacturing line as suggested in FIG. 12, cellulose fibers 49 may also be stratified by fiber type (e.g., species of source of cellulose fiber, cellulose fiber processing or treatment differences, etc.) or size The advantages thereby provided are as follows: As noted, AGM is relatively very highly absorbent as compared with the other constituents contemplated herein, and thereby contribute substantially to absorption capacity. However, as AGM particles absorb aqueous fluid and swell, an accumulation of them is susceptible to gel-blocking if their numerical density is too great, compromising the ability of the structure to distribute fluid to dry regions thereof. On the other hand, it would be desirable, if possible, to locate some AGM particles beneath but proximate overlying layers such as a topsheet 20 and/or acquisition layer 41, so that they are positioned to contact and draw fluid from these overlying layers and enable the absorbent article to continue to effectively receive and contain successive discharges of fluid. Advantageously, relatively larger AGM particles, when distributed relatively more distantly from one another in second zone 46 as suggested in FIGS. 6-10, are substantially less susceptible to gel blocking, while still being in a position to draw fluid from overlying layer(s). It can be appreciated from FIG. 6 that the combination of larger-sized filaments and larger-sized AGM particles in second zone 46 result in larger intra-filament/intra-particle spaces 63a, while the particles are effectively trapped and held within the matrix created by the accumulated larger filaments. The larger spaces 63a make second zone 46 better suited to receive and distribute rapidly discharged fluid along x-, y- and z-directions, while the trapped AGM particles enhance the ability of second zone 46 to draw fluid from overlying layer(s). In a complementary fashion, the closer spacing of smaller filaments and smaller AGM particles in first zone 45 result in smaller intra-filament/intra-particle spaces 63b, providing for slower more controlled distribution, but relatively greater absorption capacity per unit structure volume as a result of the relatively increased amount of surface area per unit weight, of the more finely divided and more numerically dense AGM particles in first zone 45. The more numerically dense accumulation of smaller filaments provide a matrix better suited to trapping and maintaining the smaller AGM particles in place within the structure, and also helps minimize gel blocking. To the extent closely-spaced AGM particles proximate the non-receiving side 44 of the structure may be more susceptible to gel blocking, it is less of a concern because their location is remote from overlying, structure that is more proximate the location of fluid discharge (i.e., at fluid receiving side 43), where fluid acquisition and distribution capability is most needed.

As a result of the referenced co-form process and apparatus, structures having features schematically depicted as examples in FIGS. 4 and 6-10 and described above may be efficiently manufactured. Thus, it is believed that structures with these features can provide an absorbent structure and/or absorbent core component that has improved fluid management characteristics, and may be efficiently and cost effectively produced in a consolidated, continuous manufacturing process.

Figure 7:
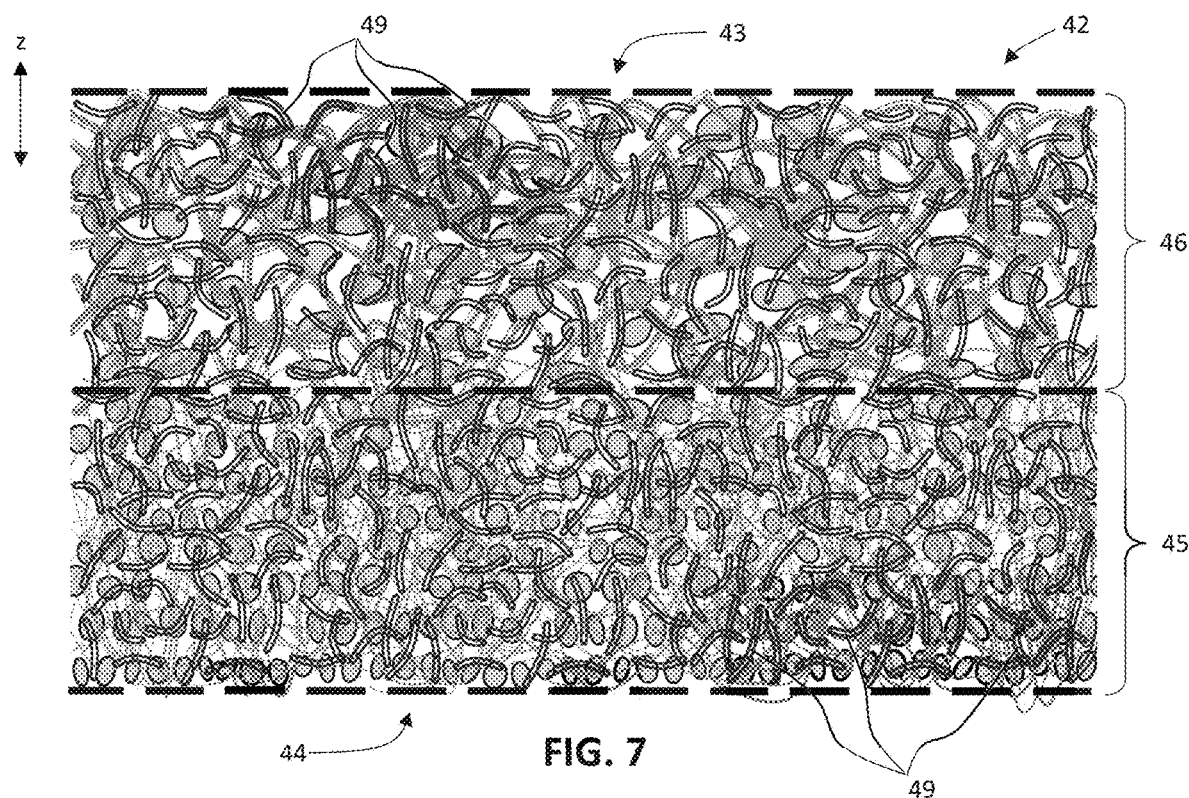
FIG. 7 is a schematic view of the combination shown in FIG. 6, further combined with an added distribution of cellulose fibers.

Referring now to FIG. 7, the referenced co-form process and apparatus may also be configured to include equipment with features to deliver, blend in and distribute cellulose fibers 49 into the absorbent structure 42. Generally, suitably selected cellulose fibers 49 (such as, for example, pulp fibers) may provide substantial added benefits to both zones 45 and 46. As a feature of their strong natural hydrophilicity, cellulose fibers effectively and rapidly wick aqueous fluid and therefore enhance fluid distribution throughout the structure, improving received fluid transport to, and contact with, surfaces of AGM particles. In suitable quantities they can also supplement the filament matrix structure, making it more effective at holding the AGM particles in place within the structure, and also providing additional material between adjacent AGM particles to maintain separation of the particles and reduce the chances for gel blocking. Finally, suitably selected cellulose fibers are relatively effective and rapid fluid absorbers themselves, thereby supplementing the absorption speed and capacity of the structure 42.

The cellulose fibers 49 may include pulp fibers. "Pulp fibers" as used herein means fibers that have been derived from plant sources. In one example within contemplation of the present disclosure, "pulp fiber" refers to papermaking fibers. In one example within contemplation of the present disclosure, a fiber may be a naturally occurring fiber, which means it is obtained from a plant source such as one or more species of trees. Such fibers are typically used in papermaking and are oftentimes referred to as papermaking fibers. Papermaking fibers useful within contemplation of the present disclosure include cellulose fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to fibrous structures made therefrom. Pulps derived from both deciduous trees (hereinafter, also referred to as "hardwood") and coniferous trees (hereinafter, also referred to as "softwood") may be utilized. Hardwood pulp fibers may be selected from the group consisting of eucalyptus fibers, acacia fibers, aspen fibers, birch fibers, maple fibers and mixtures thereof. Softwood fibers may be selected from the group consisting of cedar fibers, fir fibers, pine fibers, spruce fibers and mixtures thereof. Hardwood and softwood fibers can be blended in a single stratum or zone, or alternatively, can be deposited in layers to provide a stratified web. Also useful within contemplation of the present disclosure are fibers derived from recycled paper, which may contain any or all of the above categories of fibers as well as other non-fibrous polymers such as fillers, softening agents, wet and dry strength agents, and adhesives used to facilitate the original papermaking.

In some examples, it may be desired to include relatively larger-size pulp fibers (such as softwood pulp fibers) in the second zone 46, and relatively smaller-size pulp fibers (such as hardwood pulp fibers) in the first zone 45. The larger fibers may be better suited to preserving larger spaces/voids within the matrix, providing for more rapid fluid acquisition and distribution capability, while the smaller fibers may be better suited for slower, controlled distribution but greater absorption capacity, and for providing a more closely-spaced matrix better suited for trapping and retaining smaller AGM particles in place within the structure 42. In one example, the fibers in the first zone 45 may include eucalyptus fibers, which are relatively fine, small and soft, and thereby help enhance absorbency and softness of the first zone 45.

In addition to the various wood pulp fibers, other cellulose or cellulose-derived fibers such as cotton, cotton linters, rayon, lyocell, viscose, rice straw, wheat straw, bamboo, and bagasse fibers are within contemplation of the present disclosure. Other sources of cellulose in the form of fibers or material that may be processed and spun into fibers include grain/cereal stalks (e.g., wheat, rye, corn, sorghum, hesperaloe funifera, etc.), kapok, milkweed, coconut husk, kenaf, jute, flax, ramie, hemp, abaca, sisal, grasses (e.g., esparto, lemon, sabia, switchgrass, etc.), and canes (e.g., bamboo, bagasse, etc.).

Figure 8:
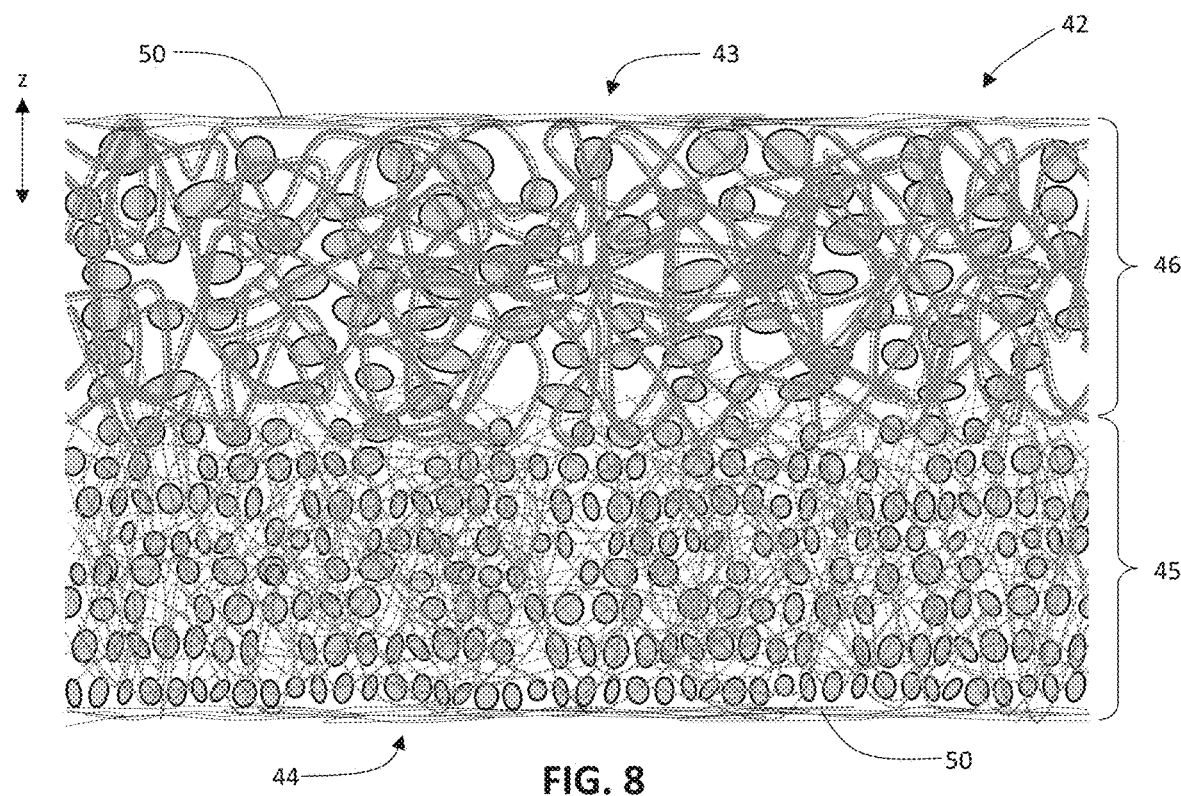
FIG. 8 is a schematic view of the combination shown in FIG. 6, depicted with added boundary layers.
Figure 9:
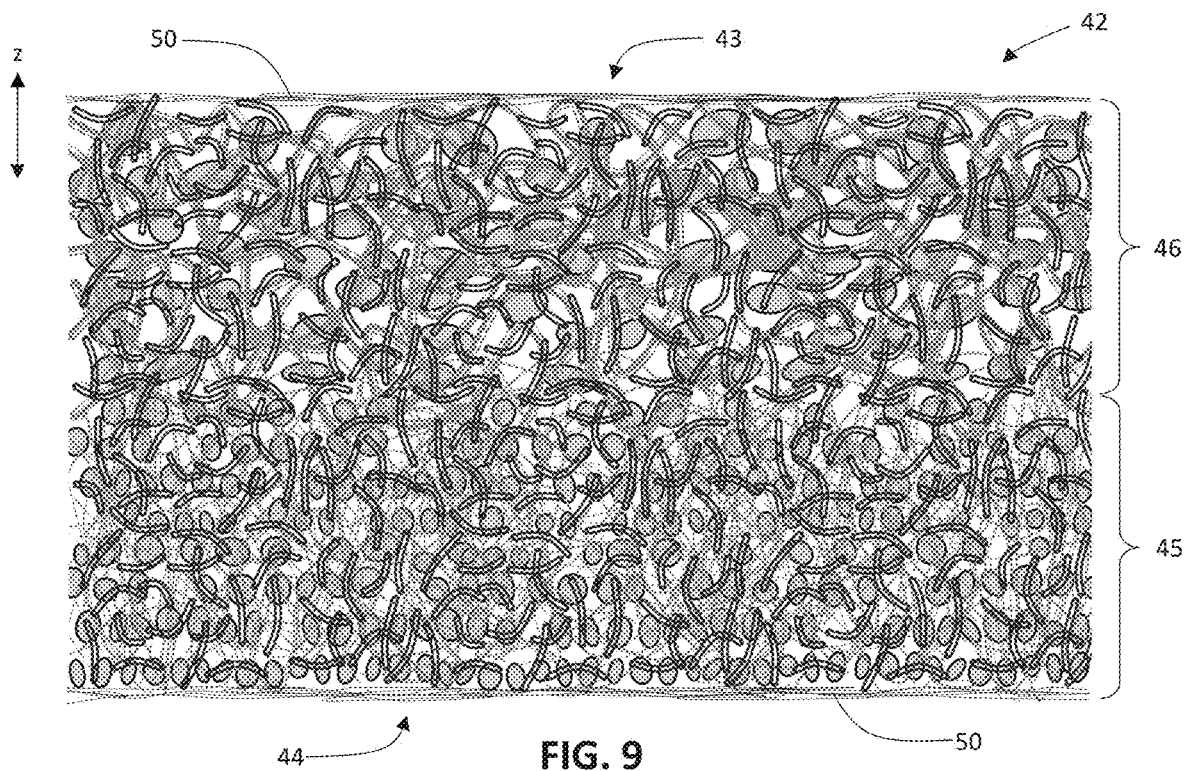
FIG. 9 is a schematic view of the combination shown in FIG. 7, depicted with added boundary layers.
Figure 10:
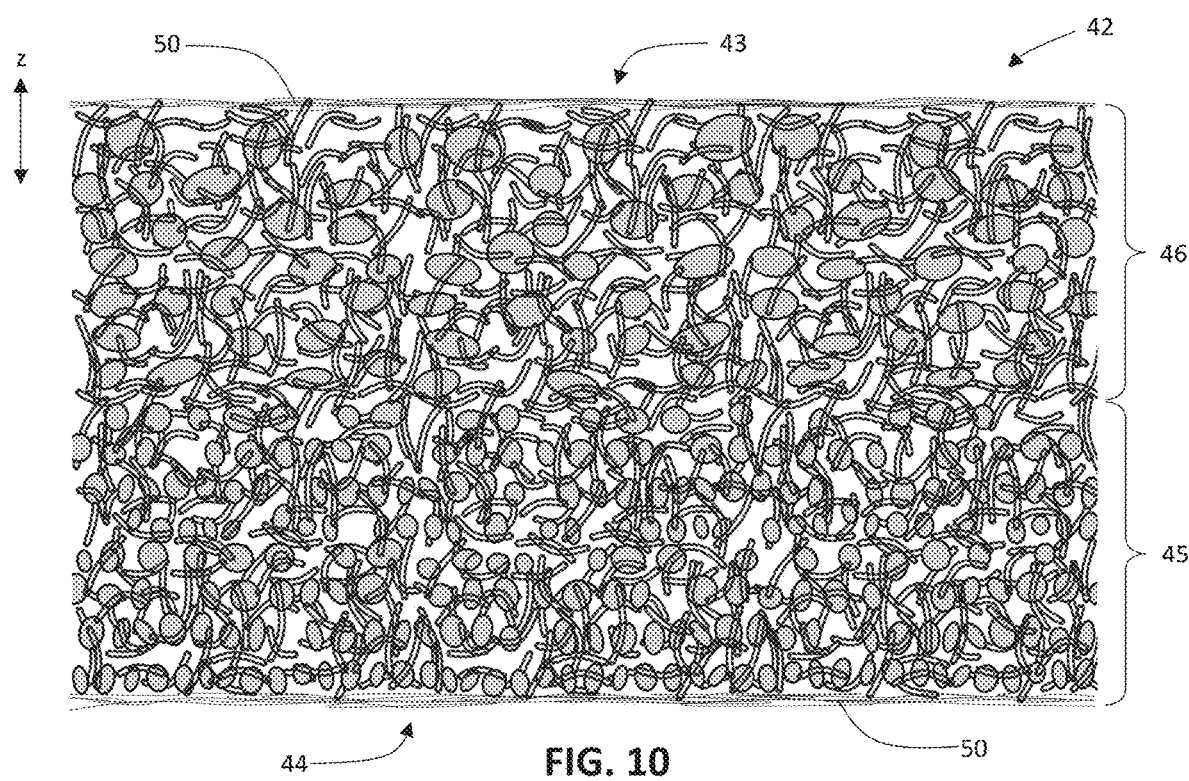
FIG. 10 is a schematic view of a combination of an arrangement of AGM particles within a portion of an absorbent structure, shown along a plane extending along a z-direction, having a variation and/or stratification in average size from a fluid receiving side to a non-receiving side of the structure, combined with an added distribution of cellulose fibers and added boundary layers.

Referring now to FIGS. 8-10, the referenced co-form process and apparatus may be configured to provide one or more boundary layers 50 at the fluid-receiving side 43 and/or non-receiving side 44. A boundary layer in some examples may be or include a substantially homogeneous, relatively low caliper (and/or low basis weight) accumulation of fine (e.g., meltblown) filaments having sufficient numerical filament density to enable the layer 50 to contain the AGM particles within the structure, i.e., to prevent AGM particles proximate the fluid-receiving side 43 and/or non-receiving side 44 from dislodging and escaping the structure 42. Thus, it may be appreciated that a boundary layer 50 overlying or superadjacent a fluid-receiving side 43 may be composed of filaments that are relatively larger and/or less numerically dense, or have a relatively lower caliper and/or basis weight, because the AGM particles proximate fluid-receiving side 43 are larger. Conversely, a boundary layer 50 underlying or subjacent a non-receiving side 44 may be composed of filaments that are relatively smaller and/or more numerically dense, or have a relatively greater caliper and/or basis weight, because the AGM particles proximate side 44 are smaller. In addition to an accumulation of filaments as described above, a boundary layer 50 may be or include a layer of woven or nonwoven fabric, or even a film. It will be appreciated that a boundary layer proximate the fluid-receiving side 43 of the absorbent structure should be configured with spaces or voids, between filaments or other constituents, that are small enough to prevent escape of AGM particles from the structure at the fluid-receiving side, but large enough to allow fluid to readily pass therethrough to the absorbent constituents within the structure proximate the boundary layer. On the other hand, fluid permeability of a boundary layer 50 proximate the non-receiving side 44 of the structure may be deemed unnecessary or even undesirable in some circumstances. Thus, a boundary layer 50 proximate the non-receiving side 44 may be or may include a fluid-impermeable nonwoven or even a fluid-impermeable film. An effectively fluid impermeable nonwoven may be formed of relatively fine (e.g. meltblown), hydrophobic filaments having a numerical density sufficient, in combination with hydrophobicity of filament surfaces, to resist passage of aqueous fluid therethrough, under ordinary conditions of use. For wearable absorbent articles such as feminine hygiene pads, diapers, absorbent pants, incontinence pads, etc., however, the boundary layer 50 proximate the non-receiving side may be configured to be vapor permeable ("breathable") for purposes of comfort and skin health, as is known in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments within contemplation of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

Non-limiting examples of structures and combinations of features contemplated herein include those set forth in the following claims.

What is claimed is:

1. An absorbent structure having a three-dimensional shape, a fluid-receiving side proximate a wearer-facing surface and a non-receiving side proximate the outward-facing surface, the non-receiving side occupying a first x-y plane, the fluid receiving side occupying a second x-y plane, a caliper measured along a z-direction relative the first and second x-y planes, a first zone constituting a first portion of the caliper proximate the non-receiving side, and a second zone constituting a second portion of the caliper proximate the fluid-receiving side, each of the first zone and the second zone comprising a co-formed blend of constituents including AGM particles and meltblown filaments, the particles in the first zone having a first average particle size, and the particles in the second zone having a second average particle size, wherein the first average particle size is smaller than the second average particle size, and wherein the AGM particles in one or both the first and second zones are stratified so as to generally exhibit a gradient of particle sizes along the z-direction, wherein the first zone has a first mass density of AGM particles therein and the second zone has a second mass density of AGM particles therein, and wherein the first mass density is greater than the second mass density, and wherein the meltblown filaments in the first zone having a first average filament size and the meltblown filaments in the second zone having a second average filament size, wherein the first average filament size is smaller than the second average filament size, and wherein the first zone has a plurality of first intra-particle spaces between the AGM particles and the meltblown filaments and the second zone has a plurality of second intra-particle spaces between the AGM particles and the meltblown filaments, and wherein the plurality of first intra particle spaces are smaller than the plurality of second intra-particle spaces; and a first boundary layer disposed on the fluid-receiving side of the absorbent structure, wherein the first boundary layer comprises filaments, wherein one or more voids are present between the filaments, wherein each of the one or more voids have a size, and wherein the size of the one or more voids is less than the first average particle size.

2. The absorbent structure of claim 1 wherein the meltblown filaments in the second zone comprise PET.

3. The absorbent structure of claim 1 wherein the co-formed blend of constituents includes cellulose fibers.

4. The absorbent structure of claim 3 wherein the cellulose fibers are present in both the first zone and the second zone.

5. The absorbent structure of claim 1 wherein the AGM particles in the first zone have an average size of 45 μm to 400 μm.

6. The absorbent structure of claim 1 wherein the AGM particles in the second zone have an average size of 45 μm to 750 μm.

7. An absorbent article comprising a liquid permeable topsheet, a liquid impermeable backsheet and an absorbent core structure disposed between the topsheet and the backsheet, the absorbent core structure comprising the absorbent structure of claim 1.

8. An absorbent structure having a three-dimensional shape, a fluid-receiving side proximate a wearer-facing surface and a non-receiving side proximate the outward-facing surface, the non-receiving side occupying a first x-y plane, the fluid receiving side occupying a second x-y plane, a caliper measured along a z-direction relative the first and second x-y planes, a first zone constituting a first portion of the caliper proximate the non-receiving side, and a second zone constituting a second portion of the caliper proximate the fluid-receiving side, each of the first zone and the second zone comprising a co-formed blend of constituents including meltblown filaments, AGM particles, and cellulose fibers, the meltblown filaments in the first zone having a first average filament size, and the meltblown filaments in the second zone having a second average filament size, wherein the second average filament size is 1.5 to 3 times greater than the first average filament size, wherein the AGM particles are present in both the first zone and the second zone, and wherein the AGM particles in the first zone have a first average particle size, and the particles in the second zone have a second average particle size, wherein the first average particle size is smaller than the second average particle size, wherein the cellulose fibers are present in at least one of the first zone and the second zone, and wherein the first zone has a plurality of first intra-particle spaces between the AGM particles and the meltblown filaments and the second zone has a plurality of second intra-particle spaces between the AGM particles and the meltblown filaments, and wherein the plurality of first intra particle spaces are smaller than the plurality of second intra-particle spaces;

a first boundary layer disposed on the fluid-receiving side of the absorbent structure, wherein the first boundary layer comprises filaments, wherein one or more voids are present between the filaments, wherein each of the one or more voids have a size, and wherein the size of the one or more voids is less than the first average particle size; and a second boundary layer disposed on the non-receiving side of the absorbent structure, wherein the second boundary layer comprises filaments, wherein one or more voids are present between the filaments, wherein each of the one or more voids have a size, and wherein the size of the one or more voids of the second boundary layer is less than the second average particle size.

9. The absorbent structure of claim 8, wherein the filaments in the second zone comprise PET.

10. The absorbent structure of claim 8 wherein the cellulose fibers are present in both the first zone and the second zone.

11. An absorbent article comprising a liquid permeable topsheet, a liquid impermeable backsheet and an absorbent core structure disposed between the topsheet and the backsheet, the absorbent core structure comprising the absorbent structure of claim 8.

* * * * *